United States Patent

Nesvadba

Patent Number: 5,369,159
Date of Patent: Nov. 29, 1994

[54] 3-(ACYLOXYPHENYL)BENZOFURAN-2-ONE STABILISERS

[75] Inventor: Peter Nesvadba, Marly, Switzerland

[73] Assignee: Ciba-Geigy Corporation, Ardsley, N.Y.

[21] Appl. No.: 64,191

[22] Filed: May 17, 1993

[30] Foreign Application Priority Data

May 22, 1992 [CH] Switzerland ............. 1652/92-3

[51] Int. Cl.⁵ .................. C08K 5/15; C09K 15/06
[52] U.S. Cl. ........................ 524/111; 252/407
[58] Field of Search .................. 524/111; 252/407

[56] References Cited

U.S. PATENT DOCUMENTS

| | | | |
|---|---|---|---|
| 3,452,094 | 6/1969 | Tanz | 564/316 |
| 4,325,863 | 4/1982 | Hinsken et al. | 624/111 |
| 4,338,244 | 7/1982 | Hinsken et al. | 524/109 |
| 5,175,312 | 12/1992 | Dubs et al. | 549/307 |
| 5,210,094 | 5/1993 | Reeve | 514/372 |

FOREIGN PATENT DOCUMENTS

| | | |
|---|---|---|
| 146269 | 6/1985 | European Pat. Off. |
| 415887 | 3/1991 | European Pat. Off. |
| 0502278 | 9/1992 | European Pat. Off. |
| 4202276 | 8/1992 | Germany |
| 1236798 | 6/1971 | United Kingdom |
| 1237764 | 6/1971 | United Kingdom |
| 2034308 | 6/1980 | United Kingdom |
| 2257140 | 1/1993 | United Kingdom |
| 2257141 | 1/1993 | United Kingdom |
| WO8001566 | 8/1980 | WIPO |

OTHER PUBLICATIONS

M. H. Hubacher, J. Org. Chem. 24, 1949 (1959).
J. Gripenberg et al., Acta Chemica Scandinavica 23, 2583 (1969).
M. Auger et al, Bull. Soc. Chim. Fr. 1970, 4024.
J. Morvan et al., Bull. Soc. Chim Fr. 1979, II, 575.
W. Bradley et al., J. Chem. Soc. 1956, 1622.
Honben-Weyl, Methoden der organischen Chemie, vol. 6/1C, 1030.
Organikum 1986, pp. 402–408.

*Primary Examiner*—Kriellion S. Morgan
*Attorney, Agent, or Firm*—Luther A. R. Hall

[57] ABSTRACT

Compounds of the formula (1)

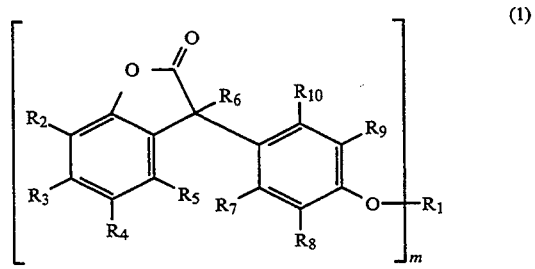

in which $R_2$, $R_3$, $R_4$ and $R_5$, independently of one another, are hydrogen, $C_1$–$C_{25}$alkyl, $C_7$–$C_9$phenylalkyl, unsubstituted or $C_1$–$C_4$alkyl-substituted phenyl, unsubstituted or $C_1$–$C_4$-alkly-substituted $C_5$–$C_8$cycloalkyl; $C_1$–$C_{18}$alkoxy, hydroxyl, $C_1$–$C_{25}$alkanoyloxy, $C_3$–$C_{25}$alkenoyloxy, $C_3$–$C_{25}$alkanoyloxy which is interrupted by oxygen, sulfur or >N—$R_{16}$; $C_6$–$C_9$cycloalkylcarbonyloxy, benzoyloxy or $C_1$–$C_{12}$alkyl-substituted benzoyloxy, where $R_{16}$ is hydrogen or $C_1$–$C_8$alkyl, or, furthermore, the radicals $R_2$ and $R_3$ or the radicals $R_4$ and $R_5$ together with the carbon atoms to which they are bound form a phenyl ring, $R_4$ is additionally —(CH$_2$)$_n$—COR$_{11}$, in which n is 0, 1 or 2, $R_{11}$ is hydroxyl,

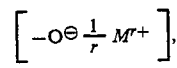

$C_1$–$C_{18}$alkoxy or

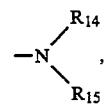

$R_{14}$ and $R_{15}$, independently of one another, are hydro- (Abstract continued on next page.)

gen or $C_1$-$C_{18}$alkyl, M is an r-valent metal cation and r is 1, 2 or 3, $R_7$, $R_8$, $R_9$ and $R_{10}$, independently of one another, are hydrogen, $C_1$-$C_4$alkyl or $C_1$-$C_4$alkoxy, with the proviso that at least one of the radicals $R_7$, $R_8$, $R_9$ and $R_{10}$ is hydrogen and, in the case where $R_3$, $R_5$, $R_6$, $R_7$ and $R_{10}$ are hydrogen, $R_4$ is additionally a radical of the formula (2)

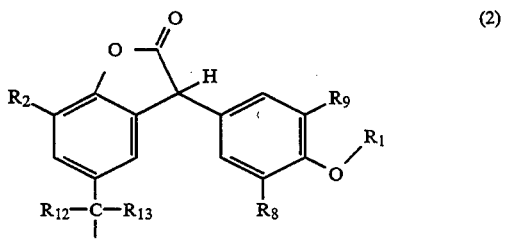

(2)

in which $R_2$, $R_8$ and $R_9$ are as defined above and $R_1$ is as defined below for m=1, and $R_{12}$ and $R_{13}$, independently of one another, are hydrogen, $C_1$-$C_{12}$alkyl or phenyl, m is 1 or 2, and, in the case where m is 1, $R_1$ is hydrogen, $C_1$-$C_{25}$alkanoyl, $C_3$-$C_{25}$alkenoyl, $C_3$-$C_{25}$alkanoyl which is interrupted by oxygen, sulfur or $>$N—$R_{16}$; $C_6$-$C_9$cycloalkylcarbonyl, benzoyl or $C_1$-$C_{12}$alkyl-substituted benzoyl, $R_{16}$ is as defined above and $R_6$ is hydrogen or a radical of the formula (3)

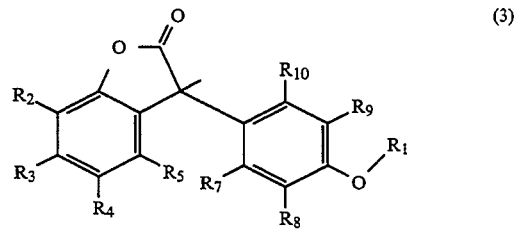

(3)

in which $R_1$, $R_2$, $R_3$, $R_4$, $R_5$, $R_7$, $R_8$, $R_9$ and $R_{10}$ are as defined above, and, in the case where m is 2, $R_1$ is

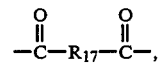

in which $R_{17}$ is a direct bond, $C_1$-$C_{18}$alkylene, $C_2$-$C_{18}$alkylene which is interrupted by oxygen, sulfur or $>$N—$R_{16}$; $C_2$-$C_{18}$alkenylene, $C_2$-$C_{20}$alkylidene, $C_7$-$C_{20}$phenylalkylidene, $C_5$-$C_8$cycloalkylene, $C_7$-$C_8$bicycloalkylene or phenylene, $R_{16}$ is as defined above and $R_6$ is hydrogen, are described as stabilizers for organic materials against oxidative, thermal or light-induced degradation.

11 Claims, No Drawings

3-(ACYLOXYPHENYL)BENZOFURAN-2-ONE STABILISERS

The present invention relates to compositions comprising an organic material, preferably a polymer, and 3-(acyloxyphenyl)benzofuran-2-ones as stabilisers, to the use of the same for the stabilisation of organic materials against oxidative, thermal or light-induced degradation and to novel 3-(acyloxyphenyl)benzofuran-2-ones.

Individual 3-(hydroxyphenyl)benzofuran-2-ones and 3-(acetoxyphenyl)benzofuran-2-ones have been described, for example, by M. H. Hubacher, J. Org. Chem. 24, 1949 (1959); J. Gripenberg et al., Acta Chemica Scandinavica 23, 2583 (1969); M. Auger et al., Bull. Soc. Chim. Fr. 1970, 4024 and J. Morvan et al., Bull. Soc. Chim. Fr. 1979, II,575.

The use of certain benzofuran-2-ones as stabilisers for organic polymers is disclosed, for example, in U.S. Pat. No. 4,325,863; U.S. Pat. No. 4,338,244 and EP-A-415 887.

It has now been found that a selected group of such benzofuran-2-ones is particularly suitable as stabilisers for organic materials sensitive to oxidative, thermal or light-induced degradation.

Accordingly, the present invention relates to compositions comprising
a) an organic material which is subject to oxidative, thermal or light-induced degradation and
b) at least one compound of the formula (1)

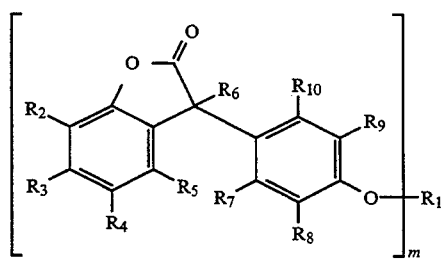
(1)

in which $R_2$, $R_3$, $R_4$ and $R_5$, independently of one another, are hydrogen, $C_1$–$C_{25}$alkyl, $C_7$–$C_9$phenylalkyl, unsubstituted or $C_1$–$C_4$alkyl-substituted phenyl, unsubstituted or $C_1$–$C_4$alkyl-substituted $C_5$–$C_8$cycloalkyl; $C_1$–$C_{18}$alkoxy, hydroxyl, $C_1$–$C_{25}$alkanoyloxy, $C_3$–$C_{25}$alkenoyloxy, $C_3$–$C_{25}$alkanoyloxy which is interrupted by oxygen, sulfur or $>$N—$R_{16}$; $C_6$–$C_9$cycloalkylcarbonyloxy, benzoyloxy or $C_1$–$C_{12}$alkyl-substituted benzoyloxy, where $R_{16}$ is hydrogen or $C_1$–$C_8$alkyl, or, furthermore, the radicals $R_2$ and $R_3$ or the radicals $R_4$ and $R_5$ together with the carbon atoms to which they are bound form a phenyl ring, $R_4$ is additionally —(CH$_2$)$_n$—COR$_{11}$, in which n is 0, 1 or 2, $R_{11}$ is hydroxyl,

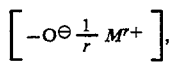, $C_1$–$C_{18}$alkoxy or

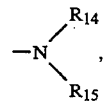

$R_{14}$ and $R_{15}$, independently of one another, are hydrogen or $C_1$–$C_{18}$alkyl, M is an r-valent metal cation and r is 1, 2 or 3, $R_7$, $R_8$, $R_9$ and $R_{10}$, independently of one another, are hydrogen, $C_1$–$C_4$alkyl or $C_1$–$C_4$alkoxy, with the proviso that at least one of the radicals $R_7$, $R_8$, $R_9$ and $R_{10}$ is hydrogen and, in the case where $R_3$, $R_5$, $R_6$, $R_7$ and $R_{10}$ are hydrogen, $R_4$ is additionally a radical of the formula (2)

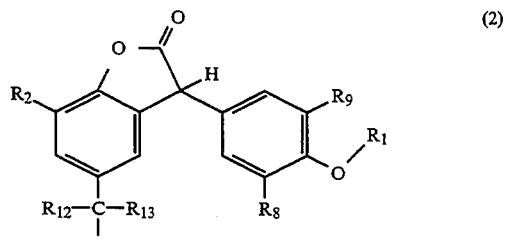
(2)

in which $R_2$, $R_8$ and $R_9$ are as defined above and $R_1$ is as defined below for m=1, and $R_{12}$ and $R_{13}$, independently of one another, are hydrogen, $C_1$–$C_{12}$alkyl or phenyl, m is 1 or 2, and,
in the case where m is 1,
$R_1$ is hydrogen, $C_1$–$C_{25}$alkanoyl, $C_3$–$C_{25}$alkenoyl, $C_3$–$C_{25}$alkanoyl which is interrupted by oxygen, sulfur or $>$N—$R_{16}$; $C_6$–$C_9$cycloalkylcarbonyl, benzoyl or $C_1$–$C_{12}$alkyl-substituted benzoyl, $R_{16}$ is as defined above and $R_6$ is hydrogen or a radical of the formula (3)

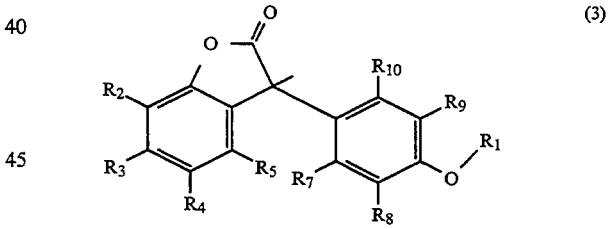
(3)

in which $R_1$, $R_2$, $R_3$, $R_4$, $R_5$, $R_7$, $R_8$, $R_9$ and $R_{10}$ are as defined above, and,
in the case where m is 2,
$R_1$ is

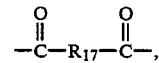

in which $R_{17}$ is a direct bond, $C_1$–$C_{18}$alkylene, $C_2$–$C_{18}$alkylene which is interrupted by oxygen, sulfur or $>$N—$R_{16}$; $C_2$–$C_{18}$alkenylene, $C_2$–$C_{20}$alkylidene, $C_7$–$C_{20}$phenylalkylidene, $C_5$–$C_8$cycloalkylene, $C_7$–$C_8$bicycloalkylene or phenylene, $R_{16}$ is as defined above and $R_6$ is hydrogen.

Alkyl of up to 25 carbon atoms is a branched or unbranched radical, for example methyl, ethyl, propyl, isopropyl, n-butyl, sec-butyl, isobutyl, tert-butyl, 2-ethylbutyl, n-pentyl, isopentyl, 1-methylpentyl, 1,3-dimethylbutyl, n-hexyl, 1-methylhexyl, n-heptyl, isoheptyl, 1,1,3,3-tetramethylbutyl, 1-methylheptyl, 3-methylheptyl, n-octyl, 2-ethylhexyl, 1,1,3-trimethylhexyl, 1,1,3,3-tetramethylpentyl, nonyl, decyl, undecyl, 1-methylundecyl, dodecyl, 1,1,3,3,5,5-hexamethylhexyl, tridecyl, tetradecyl, pentadecyl, hexadecyl, heptadecyl, octadecyl, eicosyl or docosyl. One of the preferred meanings of $R_2$ and $R_4$ is, for example, $C_1$–$C_{18}$alkyl. A particularly preferred meaning of $R_4$ is $C_1$–$C_4$alkyl.

Examples of $C_7$–$C_9$phenylalkyl are benzyl, α-methylbenzyl, α,α-dimethylbenzyl and 2-phenylethyl. Benzyl is preferred.

Examples of $C_1$–$C_4$alkyl-substituted phenyl, which preferably contains 1 to 3, in particular 1 or 2, alkyl groups, are o-, m- or p-methylphenyl, 2,3-dimethylphenyl, 2,4-dimethylphenyl, 2,5-dimethylphenyl, 2,6-dimethylphenyl, 3,4-dimethylphenyl, 3,5-dimethylphenyl, 2-methyl-6-ethylphenyl, 4-tert-butylphenyl, 2-ethylphenyl and 2,6-diethylphenyl.

Examples of unsubstituted or $C_1$–$C_4$alkyl-substituted $C_5$–$C_8$cycloalkyl are cyclopentyl, methylcyclopentyl, dimethylcyclopentyl, cyclohexyl, methylcyclohexyl, dimethylcyclohexyl, trimethylcyclohexyl, tert-butylcycloheptyl, cycloheptyl and cyclooctyl. Cyclohexyl and tert-butylcyclohexyl are preferred.

Alkoxy of up to 18 carbon atoms is a branched or unbranched radical, for example methoxy, ethoxy, propoxy, isopropoxy, n-butoxy, isobutoxy, pentoxy, isopentoxy, hexoxy, heptoxy, octoxy, decyloxy, tetradecyloxy, hexadecyloxy or octadecyloxy.

Alkanoyloxy of up to 25 carbon atoms is a branched or unbranched radical, for example formyloxy, acetyloxy, propionyloxy, butanoyloxy, pentanoyloxy, hexanoyloxy, heptanoyloxy, octanoyloxy, nonanoyloxy, decanoyloxy, undecanoyloxy, dodecanoyloxy, tridecanoyloxy, tetradecanoyloxy, pentadecanoyloxy, hexadecanoyloxy, heptadecanoyloxy, octadecanoyloxy, eicosanoyloxy or docosanoyloxy.

Alkenoyloxy of 3 to 25 carbon atoms is a branched or unbranched radical, for example propenoyloxy, 2-butenoyloxy, 3-butenoyloxy, isobutenoyloxy, n-2,4-pentadienoyloxy, 3-methyl-2-butenoyloxy, n-2-octenoyloxy, n-2-dodecenoyloxy, iso-dodecenoyloxy, oleoyloxy, n-2-octadecenoyloxy or n-4-octadecenoyloxy.

Examples of $C_3$–$C_{25}$alkanoyloxy which is interrupted by oxygen, sulfur or >N–$R_{16}$ are $CH_3$–O–$CH_2COO$–, $CH_3$–S–$CH_2COO$–, $CH_3$–NH–$CH_2COO$–, $CH_3$–N($CH_3$)–$CH_2COO$–, $CH_3$–O–$CH_2CH_2$–O–$CH_2COO$–, $CH_3$–(O–$CH_2CH_2$–)$_2$O–$CH_2COO$–, $CH_3$–(O–$CH_2CH_2$–)$_3$O–$CH_2COO$– and $CH_3$–(O–$CH_2CH_2$–)$_4$O–$CH_2COO$–.

Examples of $C_6$–$C_9$cycloalkylcarbonyloxy are cyclopentylcarbonyloxy, cyclohexylcarbonyloxy, cycloheptylcarbonyloxy and cyclooctylcarbonyloxy. Cyclohexylcarbonyloxy is preferred.

Examples of $C_1$–$C_{12}$alkyl-substituted benzoyloxy are o-, m- or p-methylbenzoyloxy, 2,3-dimethylbenzoyloxy, 2,4-dimethylbenzoyloxy, 2,5-dimethylbenzoyloxy, 2,6-dimethylbenzoyloxy, 3,4-dimethylbenzoyloxy, 3,5-dimethylbenzoyloxy, 2-methyl-6-ethylbenzoyloxy, 4-tert-butylbenzoyloxy, 2-ethylbenzoyloxy, 2,4,6-trimethylbenzoyloxy, 2,6-dimethyl-4-tert-butylbenzoyloxy and 3,5-di-tert-butylbenzoyloxy.

Alkanoyl of up 25 carbon atoms is a branched or unbranched radical, for example formyl, acetyl, propionyl, butanoyl, pentanoyl, hexanoyl, heptanoyl, octanoyl, nonanoyl, decanoyl, undecanoyl, dodecanoyl, tridecanoyl, tetradecanoyl, pentadecanoyl, hexadecanoyl, heptadecanoyl, octadecanoyl, eicosanoyl or docosanoyl. A preferred meaning of $R_1$ is $C_1$–$C_{18}$alkanoyl. A particularly preferred meaning of $R_1$ is $C_5$–$C_{10}$alkanoyl branched in the α position. A specifically preferred meaning of $R_1$ is pivaloyl and 2,2-dimethyloctanoyl.

Alkenoyl of 3 to 25 carbon atoms is a branched or unbranched radical, for example propenoyl, 2-butenoyl, 3-butenoyl, isobutenoyl, n-2,4-pentadienoyl, 3-methyl-2-butenoyl, n-2-octenoyl, n-2-dodecenoyl, iso-dodecenoyl, oleoyl, n-2-octadecenoyl or n-4-octadecenoyl.

Examples of $C_3$–$C_{25}$alkanoyl which is interrupted by oxygen, sulfur or >N–$R_{16}$ are $CH_3$–O–$CH_2CO$–, $CH_3$–S–$CH_2CO$–, $CH_3$–NH–$CH_2CO$–, $CH_3$–N($CH_3$)–$CH_2CO$–, $CH_3$–O–$CH_2CH_2$–O–$CH_2CO$–, $CH_3$–(O–$CH_2CH_2$–)$_2$O–$CH_2CO$–, $CH_3$–(O–$CH_2CH_2$–)$_3$O–$CH_2CO$– and $CH_3$–(O–$CH_2CH_2$–)$_4$O–$CH_2CO$–. Methoxyacetyl is preferred.

Examples of $C_6$–$C_9$cycloalkylcarbonyl are cyclopentylcarbonyl, cyclohexylcarbonyl, cycloheptylcarbonyl and cyclooctylcarbonyl. Cyclohexylcarbonyl is preferred.

Examples of $C_1$–$C_{12}$alkyl-substituted benzoyl are o-, m- or p-methylbenzoyl, 2,3-dimethylbenzoyl, 2,4-dimethylbenzoyl, 2,5-dimethylbenzoyl, 2,6-dimethylbenzoyl, 3,4-dimethylbenzoyl, 3,5-dimethylbenzoyl, 2-methyl-6-ethylbenzoyl, 4-tert-butylbenzoyl, 2-ethylbenzoyl, 2,4,6-trimethylbenzoyl, 2,6-dimethyl-4-tert-butylbenzoyl and 3,5-ditert-butylbenzoyl.

Alkylene of up to 18 carbon atoms is a branched or unbranched radical, for example methylene, ethylene, propylene, trimethylene, tetramethylene, pentamethylene, hexamethylene, heptamethylene, octamethylene, decamethylene, dodecamethylene or octadecamethylene. $C_1$–$C_8$Alkylene is preferred.

Examples of $C_2$–$C_{18}$alkylene which is interrupted by oxygen, sulfur or >N–$R_{16}$ are –$CH_2$–O–$CH_2$–, –$CH_2$–S–$CH_2$–, –$CH_2$–NH–$CH_2$–, –$CH_2$–N($CH_3$)–$CH_2$–, –$CH_2$–O–$CH_2CH_2$–O–$CH_2$–, –$CH_2$–(O–$CH_2CH_2$–)$_2$O–$CH_2$–, –$CH_2$–(O–$CH_2CH_2$–)$_3$O–$CH_2$– and –$CH_2$–(O–$CH_2CH_2$–)$_4$O–$CH_2$–.

Examples of alkenylene of 2 to 18 carbon atoms are vinylene, methylvinylene, octenylethylene and dodecenylethylene. $C_2$–$C_8$Alkenylene is preferred.

Examples of alkylidene of 2 to 20 carbon atoms are ethylidene, propylidene, butylidene, pentylidene, 4-methylpentylidene, heptylidene, nonylidene, tridecylidene, nonadecylidene, 1-methylethylidene, 1-ethylpropylidene and 1-ethylpentylidene. $C_2$–$C_8$Alkylidene is preferred.

Examples of phenylalkylidene of 7 to 20 carbon atoms are benzylidene, 2-phenylethylidene and 1-phenyl-2-hexylidene. $C_7$–$C_9$phenylalkylidene is preferred.

$C_5$–$C_8$Cycloalkylene is a saturated hydrocarbon group having two free valences and at least one ring unit and is, for example, cyclopentylene, cyclohexylene, cycloheptylene or cyclooctylene. Cylcohexylene is preferred.

Examples of $C_7$–$C_8$bicycloalkylene are bicycloheptylene and bicyclooctylene.

Examples of phenylene are 1,2-, 1,3- and 1,4-phenylene. 1,2- and 1,4-phenylene are preferred.

A mono-, di- or trivalent metal cation is preferably an alkali metal cation, alkaline earth metal cation or aluminium cation, for example Na+, K+, Mg++, Ca++ or Al+++.

Of interest are compositions containing compounds of the formula (1) in which $R_2$, $R_3$, $R_4$ and $R_5$, independently of one another, are hydrogen, $C_1$-$C_{18}$alkyl, benzyl, phenyl, $C_5$-$C_8$-cycloalkyl, $C_1$-$C_8$alkoxy, hydroxyl, $C_1$-$C_{18}$alkanoyloxy, $C_3$-$C_{18}$alkenoyloxy or benzoyloxy, $R_4$ is additionally —$(CH_2)_n$—$COR_{11}$, and, in the case where m is 1, $R_1$ is hydrogen, $C_1$-$C_{18}$alkanoyl, $C_3$-$C_{18}$alkenoyl, $C_3$-$C_{18}$alkanoyl which is interrupted by oxygen, sulfur or >N—$R_{16}$; $C_6$-$C_9$cycloalkylcarbonyl, benzoyl or $C_1$-$C_8$alkyl-substituted benzoyl, $R_{16}$ is as defined above and, in the case where m is 2, $R_1$ is

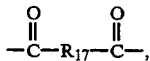

in which $R_{17}$ is a direct bond, $C_1$-$C_{12}$alkylene, $C_2$-$C_{12}$alkylene which is interrupted by oxygen, sulfur or >N—$R_{16}$; $C_2$-$C_{12}$alkenylene, $C_2$-$C_{12}$alkylidene, $C_7$-$C_{12}$phenylalkylidene, $C_5$-$C_8$cycloalkylene or phenylene and $R_{16}$ is as defined above.

Preference is given to compositions in which in formula (1) at least two of the radicals $R_2$, $R_3$, $R_4$ and $R_5$ are hydrogen.

Preference is also given to compositions in which in formula (1) $R_3$ and $R_5$ are hydrogen.

Preference is likewise given to compositions in which in formula (1) $R_3$, $R_5$, $R_7$ and $R_{10}$, independently of one another, are hydrogen or $C_1$-$C_4$alkyl, $R_2$ is hydrogen or $C_1$-$C_{18}$alkyl, $R_4$ is hydrogen, $C_1$-$C_{12}$alkyl, $C_1$-$C_8$alkoxy, hydroxyl or —$(CH_2)_n$—$COR_{11}$, in which n is 0, 1 or 2, $R_{11}$ is hydroxyl or $C_1$-$C_{12}$alkoxy, and, in the case where m is 1, $R_1$ is hydrogen, $C_1$-$C_{18}$alkanoyl, $C_3$-$C_{18}$alkanoyl which is interrupted by oxygen; or $C_3$-$C_{18}$alkenoyl, and, in the case where m is 2, $R_1$ is

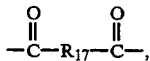

in which $R_{17}$ is $C_1$-$C_8$alkylene, $C_2$-$C_8$alkenylene, $C_2$-$C_8$alkylidene, $C_7$-$C_9$phenylalkylidene, cyclohexylene or phenylene.

Preference is also given to compositions in which in formula (1) $R_2$ is hydrogen or $C_1$-$C_{14}$alkyl, $R_3$ and $R_5$ are hydrogen, $R_4$ is hydrogen, hydroxyl, $C_1$-$C_4$alkyl, $C_1$-$C_4$alkoxy or —$(CH_2)_n$—$COR_{11}$, in which n is 2 and $R_{11}$ is hydroxyl, $R_7$, $R_8$, $R_9$ and $R_{10}$, independently of one another, are $C_1$-$C_4$alkyl or $C_1$-$C_4$alkoxy, with the proviso that at least one of the radicals $R_7$, $R_8$, $R_9$ or $R_{10}$ is hydrogen, m is 1 and $R_1$ is hydrogen, $C_1$-$C_{18}$alkanoyl, $C_3$-$C_8$alkanoyl which is interrupted by oxygen; or is $C_3$-$C_4$alkenoyl and $R_6$ is hydrogen or a radical of the formula (3)

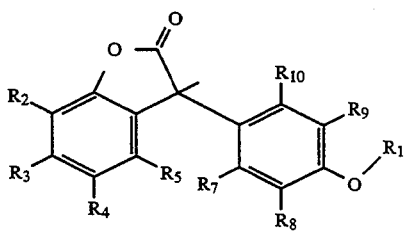

(3)

in which $R_1$, $R_2$, $R_3$, $R_4$, $R_5$, $R_7$, $R_8$, $R_9$ and $R_{10}$ are as defined above.

Particular preference is given to compositions in which in formula (1) $R_2$ is hydrogen or $C_1$-$C_{14}$alkyl, $R_3$, $R_5$, $R_6$, $R_7$ and $R_{10}$ are hydrogen, $R_4$ is hydrogen or $C_1$-$C_4$alkyl, $R_8$ and $R_9$, independently of one another, are hydrogen, $C_1$-$C_4$alkyl or $C_1$-$C_4$alkoxy, m is 1 and $R_1$ is $C_1$-$C_{10}$alkanoyl or $C_3$-$C_4$alkenoyl.

The compounds according to the invention of the formula (1) are suitable for the stabilisation of organic materials against oxidative, thermal and/or light-induced degradation.

Examples of such materials are:

1. Polymers of monoolefins and diolefins, for example polypropylene, polyisobutylene, polybut-1-ene, poly-4-methylpent-1-ene, polyisoprene or polybutadiene, as well as polymers of cycloolefins, for instance of cyclopentene or norbornene, polyethylene (which optionally can be crosslinked), for example high density polyethylene (HDPE), low density polyethylene (LDPE), linear low density polyethylene (LLDPE), branched low density polyethylene (BLDPE).

Polyolefins, i.e. the polymers of monoolefins exemplified in the preceding paragraph, preferably polyethylene and polypropylene, can be prepared by different, and especially by the following, methods:

a) radical polymerisation (normally under high pressure and at elevated temperature).

b) catalytic polymerisation using a catalyst that normally contains one or more than one metal of groups IVb, Vb, VIb or VIII of the Periodic Table. These metals usually have one or more than one ligand, typically oxides, halides, alcoholates, esters, ethers, amines, alkyls, alkenyls and/or aryls that may be either π- or σ-coordinated. These metal complexes may be in the free form or fixed on substrates, typically on activated magnesium chloride, titanium(III) chloride, alumina or silicon oxide. These catalysts may be soluble or insoluble in the polymerisation medium. The catalysts can be used by themselves in the polymerisation or further activators may be used, typically metal alkyls, metal hydrides, metal alkyl halides, metal alkyl oxides or metal alkyloxanes, said metals beeing elements of groups Ia, IIa and/or IIIa of the Periodic Table. The activators may be modified conveniently with further ester, ether, amine or silyl ether groups. These catalyst stystems are usually termed Phillips, Standard Oil Indiana, Ziegler (-Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but1ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate copolymers and their copolymers with carbon monoxide or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1) above, for example polypropylene/ethylene-propylene copolymers, LDPE/ethylene-vinyl acetate copolymers (EVA), LDPE/ethylene-acrylic acid copolymers (EAA), LLDPE/EVA, LLDPE/EAA and alternating or random polyalkylene/carbon monoxide copolymers and mixtures thereof with other polymers, for example polyamides.

4. Hydrocarbon resins (for example $C_5$–$C_9$) including hydrogenated modifications thereof (e.g. tackifiers) and mixtures of polyalkylenes and starch.

5. Polystyrene, poly(p-methylstyrene), poly($\alpha$-methylstyrene).

6. Copolymers of styrene or $\alpha$-methylstyrene with dienes or acrylic derivatives, for example styrene/butadiene, styrene/acrylonitrile, styrene/alkyl methacrylate, styrene/butadiene/alkyl acrylate, styrene/butadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer; and block copolymers of styrene such as styrene/butadiene/styrene, styrene/isoprene/styrene, styrene/ethylene/butylene/styrene or styrene/ethylene/propylene/styrene.

7. Graft copolymers of styrene or $\alpha$-methylstyrene, for example styrene on polybutadiene, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or AES polymers.

8. Halogen-containing polymers such as polychloroprene, chlorinated rubbers, chlorinated or sulfochlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloride/vinylidene chloride, vinyl chloride/vinyl acetate or vinylidene chloride/vinyl acetate copolymers.

9. Polymers derived from $\alpha,\beta$-unsaturated acids and derivatives thereof such as polyacrylates and polymethacrylates; polymethyl methacrylates, polyacrylamides and polyacrylonitriles, impact-modified with butyl acrylate.

10. Copolymers of the monomers mentioned under 9) with each other or with other unsaturated monomers, for example acrylonitrile/butadiene copolymers, acrylonitrile/alkyl acrylate copolymers, acrylonitrile/alkoxyalkyl acrylate or acrylonitrile/vinyl halide copolymers or acrylonitrile/alkyl methacrylate/butadiene terpolymers.

11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in 1) above.

12. Homopolymers and copolymers of cyclic ethers such as polyalkylene glycols, polyethylene oxide, polypropylene oxide or copolymers thereof with bisglycidyl ethers.

13. Polyacetals such as polyoxymethylene and those polyoxymethylenes which contain ethylene oxide as a comonomer; polyacetals modified with thermoplastic polyurethanes, acrylates or MBS.

14. Polyphenylene oxides and sulfides, and mixtures of polyphenylene oxides with styrene polymers or polyamides.

15. Polyurethanes derived from hydroxyl-terminated polyethers, polyesters or polybutadienes on the one hand and aliphatic or aromatic polyisocyanates on the other, as well as precursors thereof.

16. Polyamides and copolyamides derived from diamines and dicarboxylic acids and/or from aminocarboxylic acids or the corresponding lactams, for example polyamide 4, polyamide 6, polyamide 6/6, 6/10, 6/9, 6/12, 4/6, 12/12, polyamide 11, polyamide 12, aromatic polyamides starting from m-xylene diamine and adipic acid; polyamides prepared from hexamethylenediamine and isophthalic off and terephthalic acid and with or without an elastomer as modifier, for example poly-2,4,4,-trimethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).

17. Polyureas, polyimides, polyamide-imides and polybenzimidazoles.

18. Polyesters derived from dicarboxylic acids and diols and/or from hydroxycarboxylic acids or the corresponding lactones, for example polyethylene terephthalate, polybutylene terephthalate, poly-1,4-dimethylolcyclohexane terephthalate and polyhydroxybenzoates, as well as block copolyether esters derived from hydroxyl-terminated polyethers; and also polyesters modified with polycarbonates or MBS.

19. Polycarbonates and polyester carbonates.

20. Polysulfoncs, polyether sulfones and polyether ketones.

21. Crosslinked polymers derived from aldehydes on the one hand and phenols, ureas and melamines on the other hand, such as phenol/formaldehyde resins, urea/formaldehyde resins and melamine/formaldehyde resins.

22. Drying and non-drying alkyd resins.

23. Unsaturated polyester resins derived from copolyesters of saturated and unsaturated dicarboxylic acids with polyhydric alcohols and vinyl compounds as crosslinking agents, and also halogen-containing modifications thereof of low flammability.

24. Crosslinkable acrylic resins derived from substituted acrylates, for example epoxy acrylates, urethane acrylates or polyester acrylates.

25. Alkyd resins, polyester resins and acrylate resins crosslinked with melamine resins, urea resins, polyisocyanates or epoxy resins.

26. Crosslinked epoxy resins derived from polyepoxides, for example from bisglycidyl ethers or from cycloaliphatic diepoxides.

27. Natural polymers such as cellulose, rubber, gelatin and chemically modified homologous derivatives thereof, for example cellulose acetates, cellulose propionates and cellulose butyrates, or the cellulose ethers such as methyl cellulose; as well as rosins and their derivatives.

28. Blends of the aforementioned polymers (polyblends), for example PP/EPDM, Polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO.

29. Naturally occurring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, typically those used as spinning compositions, as well as aqueous emulsions of such materials.

30. Aqueous emulsions or natural or synthetic rubber, e.g. natural latex or latices of carboxylated styrene-/butadiene copolymers.

Preferred organic materials are polymers, for example synthetic polymers, in particular thermoplastic polymers. Polyolefins and polyurethanes are particularly preferred. Examples of preferred polyolefins are polypropylene or polyethylene.

The compositions according to the invention also serve for the preparation of polyurethanes, in particular for the preparation of flexible polyurethane foams. The compositions according to the invention and the products prepared therefrom are effectively protected against degradation. In particular, scorching during foam manufacture is avoided.

The polyurethanes are obtained, for example, by reaction of polyethers, polyesters and polybutadienes containing terminal hydroxyl groups with aliphatic or aromatic polyisocyanates.

Polyethers containing terminal hydroxyl groups are known and are prepared, for example, by polymerisation of epoxides, such as ethylene oxide, propylene oxide, butylene oxide, tetrahydrofuran, styrene oxide or epichlorohydrin with themselves, for example in the presence of $BF_3$, or by addition reaction of these epoxides, if desired in a mixture or in succession, with starting components containing reactive hydrogen atoms, such as water, alcohols, ammonia or amines, for example ethylene glycol, 1,3- and 1,2-propylene glycol, trimethylolpropane, 4,4'-dihydroxydiphenylpropane, aniline, ethanolamine or ethylenediamine. According to the invention, sucrose polyethers are also suitable. In many cases, those polyethers are preferred which predominantly (up to 90% by weight, relative to all OH groups present in the polyether) contain primary OH groups. Polyethers modified by vinyl polymers, such as are formed, for example, by polymerisation of styrene and acrylonitrile in the presence of polyethers, are also suitable, as are polybutadienes containing OH groups.

These compounds generally have molecular weights of 400–10,000. They are polyhydroxy compounds, in particular compounds containing two to eight hydroxyl groups, specifically those of molecular weight 800 to 10,000, preferably 1000 to 6000, for example polyethers containing at least two, usually 2 to 8, but preferably 2 to 4, hydroxyl groups, such as are known per se for the preparation of homogeneous and of cellular polyurethanes.

It is of course also possible to use mixtures of the abovementioned compounds which contain at least two hydrogen atoms which are reactive with isocyanates, in particular those having a molecular weight of 400–10,000.

Suitable polyisocyanates are aliphatic, cycloaliphatic, araliphatic, aromatic and heterocyclic polyisocyanates, for example ethylene diisocyanate, 1,4-tetramethylene diisocyanate, 1,6-hexamethylene diisocyanate, 1,12-diisocyanatododecane, 1,3-cyclobutane diisocyanate, 1,3- and 1,4-cyclohexane diisocyanate and any desired mixtures of these isomers, 1-isocyanato-3,3,5-trimethyl-5-isocyanatomethylcyclohexane, 2,4- and 2,6-hexahydrotoluylene diisocyanate and any desired mixtures of these isomers, 1,3- and/or 1,4-hexahydrophenylene diisocyanate, 2,4'- and/or 4,4'-diisocyanatoperhydrodiphenylmethane, 1,3- and 1,4-phenylene diisocyanate, 2,4- and 2,6-toluylene diisocyanate and any desired mixtures of these isomers, 2,4'- and/or 4,4'-diisocyanatodiphenylmethane, 1,5-naphthylene diisocyanate, 4,4',4''-triisocyanatotriphenylmethane, polyphenylpolymethylene polyisocyanates, such as are obtained by aniline/formaldehyde condensation, followed by phosgenation, m- and p-isocyanatophenylsulfonyl isocyanates, perchlorinated aryl polyisocyanates, polyisocyanates containing carbodiimide groups, polyisocyanates containing allophanate groups, polyisocyanates containing isocyanurate groups, polyisocyanates containing urethane groups, polyisocyanates containing acylated urea groups, polyisocyanates containing biuret groups, polyisocyanates containing ester groups, reaction products of the abovementioned isocyanates with acetals, and polyisocyanates containing polymeric fatty acid radicals.

It is also possible to use the isocyanato-containing distillation residues formed in the industrial preparation of isocyanates, if desired dissolved in one or more of the abovementioned polyisocyanates. Furthermore, it is possible to use any desired mixtures of the abovementioned polyisocyanates.

Particular preference is usually given to the industrially readily accessible polyisocyanates, for example 2,4- and 2,6-toluylene diisocyanate and any desired mixtures of these isomers ("TDI"), polyphenyl polymethylene polyisocyanates such as are prepared by aniline/formaldehyde condensation, followed by phosgenation ("crude MDI"), and polyisocyanates containing carbodiimide groups, urethane groups, allophanate groups, isocyanurate groups, urea groups or biuret groups ("modified polyisocyanates").

The activity of the compounds according to the invention against thermal and oxidative degradation, especially upon thermal stress, such as occurs during processing of thermoplastics, may be mentioned in particular. Accordingly, the compounds according to the invention are highly suitable for use as processing stabilisers.

Preferably, the compounds of the formula (1) are added to the material to be stabilised in amounts of 0.0005 to 5%, in particular 0.001 to 2%, for example 0.01 to 2%, relative to the weight of the organic material to be stabilised.

The compositions according to the invention can contain, in addition to the compounds of the formula (1), further costabilisers, for example the ones listed below:

1. Antioxidants 1.1. Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, 2,6-di-nonyl-4-methylphenol, 2,4-dimethyl-6-(1'-methylundec-1'-yl)phenol, 2,4-dimethyl-6-(1'-methylheptadec-1'-yl)phenol, 2,4-dimethyl-6-(1'-methyltridec-1'-yl)phenol and mixtures thereof.

1.2. Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6-di-dodecylthiomethyl-4-nonylphenol.

1.3. Hydroquinones and alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis-(3,5-di-tert-butyl-4-hydroxyphenyl) adipate.

1.4. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis-(3,6-di-sec-amylphenol), 4,4'-bis-(2,6-dimethyl-4-hydroxyphenyl) disulfide.

1.5. Alkylidenebisphenols, for example 2,2'-methylenebis(6-tert-butyl-4-methylphenol), 2,2'-methylenebis(6-tert-butyl-4-ethylphenol), 2,2'-methylenebis[4-methyl-6-(α-methylcyclohexyl)-phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methyl-phenyl)-3-n-dodecylmercaptobutane, ethylene glycol bis[3,3-bis(3'-tert-butyl-4'-hydroxyphenyl)butyrate], bis(3-tert-butyl-4-hydroxy-5-methyl-phenyl)dicyclopentadiene, bis[2-(3'-tert-butyl-2'-hydroxy-5'-methylbenzyl)-6-tert-butyl-4-methylphenyl]terephthalate, 1,1-bis-(3,5-dimethyl-2-hydroxyphenyl)butane, 2,2-bis-(3,5-di-tert-butyl-4-hydroxyphenyl)propane, 2,2-bis-(5-tert-butyl-4-hydroxy2-methylphenyl)-4-n-dodecylmercaptobutane, 1,1,5,5-tetra-(5-tert-butyl-4-hydroxy2-methylphenyl)pentane.

1.6. O—, N— and S-benzyl compounds, for example 3,5,3',5'-tetra-tert-butyl-4,4'-dihydroxydibenzyl ether, octadecyl-4-hydroxy-3,5-dimethylbenzylmercaptoacetate, tris-(3,5-di-tert-butyl-4-hydroxybenzyl)amine, bis(4-tert-butyl-3-hydroxy-2,6-dimethylbenzyl)dithioterephthalate, bis(3,5-di-tert-butyl-4-hydroxybenzyl)sulfide, isooctyl-3,5di-tert-butyl-4-hydroxybenzylmercaptoacetate.

1.7. Hydroxybenzylated malonates, for example dioctadecyl-2,2-bis-(3,5-di-tert-butyl-2-hydroxybenzyl)-malonate, di-octadecyl-2-(3-tert-butyl-4-hydroxy-5-methylbenzyl)-malonate, di-dodecyl-mercaptoethyl-2,2-bis-(3,5-di-tert-butyl-4-hydroxybenzyl)malonate, bis[4-(1,1,3,3-tetramethylbutyl)-phenyl]-2,2-bis(3,5-di-tert-butyl-4-hydroxybenzyl)-malonate.

1.8. Aromatic hydroxybenzyl compounds, for example 1,3,5-tris-(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol.

1.9. Triazine Compounds, for example 2,4-bis(octylmercapto)-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris(3,5-di-tert-butyl-4-hydroxyphenoxy)-1,2,3-triazine, 1,3,5-tris(3,5-di-tert-butyl-4-hydroxybenzyl)isocyanurate, 1,3,5-tris(4-tert-butyl-3-hydroxy-2,6-dimethylbenzyl)isocyanurate, 2,4,6-tris(3,5-di-tert-butyl-4-hydroxyphenylethyl)-1,3,5-triazine, 1,3,5-tris(3,5-di-tert-butyl-4-hydroxyphenylpropionyl)-hexahydro-1,3,5-triazine, 1,3,5-tris(3,5-dicyclohexyl-4-hydroxybenzyl)isocyanurate.

1.10. Benzylphosphonates, for example dimethyl-2,5-di-tert-butyl-4-hydroxybenzylphosphonate, diethyl-3,5-di-tert-butyl-4-hydroxybenzylphosphonate, dioctadecyl3,5-di-tert-butyl-4-hydroxybenzylphosphonate, dioctadecyl-5-tert-butyl-4-hydroxy3-methylbenzylphosphonate, the calcium salt of the monoethyl ester of 3,5-di-tert-butyl-4-hydroxybenzylphosphonic acid.

1.11. Acylaminophenols, for example 4-hydroxylauranilide, 4-hydroxystearanilide, octyl N-(3,5-di-tert-butyl-4-hydroxyphenyl)carbamate.

1.12. Esters of β-(3,5-di-tert-butyl-4-hydroxyphenyl)-propionic acid with mono- or polyhydric alcohols, e.g. with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.13. Esters of β-(5-tert-butyl-4-hydroxy-3-methylphenyl)propionic acid with mono- or polyhydric alcohols, e.g. with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-

1.14 Esters of β-(3,5-dicyclohexyl-4-hydroxyphenyl)-propionic acid with mono- or polyhydric alcohols, e.g. with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.15 Esters of 3,5-di-tert-butyl-4-hydroxyphenyl acetic acid with mono- or polyhydric alcohols, e.g. with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2] octane.

1.16. Amides of β-(3,5-di-tert-butyl-4-hydroxyphenyl)propionic acid e.g. N, N'-bis(3,5-di-tert-butyl-4-hydroxyphenylpropionyl)hexamethylenediamine, N,N'-bis(3,5-di-tert-butyl-4-hydroxyphenylpropionyl)trimethylenediamine, N,N'-bis(3,5-di-tert-butyl-4-hydroxyphenylpropionyl)hydrazine.

2. UV Absorbers and Light Stabilisers 2.1. 2-(2'-Hydroxyphenyl)benzotriazoles, for example 2-(2'-hydroxy-5'-methylphenyl)benzotriazole, 2-(3',5'-di-tert-butyl-2'-hydroxyphenyl)benzotriazole, 2-(5'-tert-butyl-2'-hydroxyphenyl)benzotriazole 2-(2'-hydroxy-5'-(1,1,3,3-tetramethylbutyl)phenyl)benzotriazole, 2-(3',5'-di-tert-butyl-2'-hydroxyphenyl)-5-chloro-benzotriazole, 2-(3'-tert-butyl-2'-hydroxy-5'-methylphenyl)-5-chloro-benzotriazole, 2-(3'-sec-butyl-5'-tert-butyl-2'-hydroxyphenyl)benzotriazole 2-(2'-hydroxy-4'-octyloxyphenyl)benzotriazole, 2-(3',5'-di-tert-amyl-2'-hydroxyphenyl)benzotriazole, 2-(3',5'-bis-(α,α-dimethylbenzyl)-2'-hydroxyphenyl)benzotriazole, mixture of 2-(3'-tert-butyl-2'-hydroxy-5'-(2-octyloxycarbonylethyl)phenyl)-5-chloro-benzotriazole, 2-(3'-tert-butyl-5'-[2-(2-ethylhexyloxy)-carbonylethyl]-2'-hydroxyphenyl)-5-chloro-benzotriazole, 2-(3'-tert-butyl-2'-hydroxy-5'-(2-methoxycarbonylethyl)phenyl)-5-chloro-benzotriazole, 2-(3'-tert-butyl-2'-hydroxy-5'-(2-methoxycarbonylethyl)phenyl)benzotriazole, 2-(3'-tert-butyl-2'-hydroxy-5'-(2-octyloxycarbonylethyl)phenyl)-benzotriazole, 2-(3'-tert-butyl-5'-[2-(2-ethylhexyloxy)carbonylethyl]-2'-hydroxyphenyl)benzotriazole, 2-(3'-dodecyl-2'-hydroxy-5'-methylphenyl)benzotriazole, and 2-(3'-tert-butyl-2'-hydroxy-5'-(2-isooctyloxycarbonylethyl)phenylbenzotriazole, 2,2'-methylene-bis[4-(1,1,3,3-tetramethylbutyl)-6-benzotriazole-2-ylphenol]; the transesterification product of 2-[3'-tert-butyl-5'-(2-methoxycarbonylethyl)-2'-hydroxyphenyl]-2H-benzotriazole with polyethylene glycol 300; [R—CH₂CH₂—COO(CH₂)₃]₂], where R=3'-tert-butyl-4'-hydroxy-5'-2H-benzotriazol-2-ylphenyl.

2.2. 2-Hydroxybenzophenones, for example the 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy derivatives.

2.3. Esters of substituted and unsubstituted benzoic acids, as for example 4-tertbutylphenyl salicylate, phenyl salicylate, octylphenyl salicylate, dibenzoyl resorcinol, bis(4-tert-butylbenzoyl) resorcinol, benzoyl resorcinol, 2,4-di-tertbutylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

2.4. Acrylates, for example ethyl α-cyano-β,β-diphenylacrylate, isooctyl α-cyano-β,β-diphenylacrylate, methyl α-carbomethoxycinnamate, methyl α-cyano-β-methyl-p-methoxycinnamate, butyl α-cyano-β-methyl-p-methoxy-cinnamate, methyl α-carbomethoxy-p-methoxycinnamate and N-(β-carbomethoxy-β-cyanovinyl)-2-methylindoline.

2.5. Nickel compounds, for example nickel complexes of 2,2'-thio-bis-[4-(1,1,3,3-tetramethylbutyl)-phenol], such as the 1:1 or 1:2 complex, with or without additional ligands such as n-butylamine, triethanolamine or N-cyclohexyldiethanolamine, nickel dibutyldithiocarbamate, nickel salts of the monoalkyl esters, e.g. the methyl or ethyl ester, of 4-hydroxy-3,5-di-tert-butylbenzylphosphonic acid, nickel complexes of ketoximes, e.g. of 2-hydroxy-4-methylphenyl undecylketoxime, nickel complexes of 1-phenyl-4-lauroyl-5-hydroxypyrazole, with or without additional ligands.

2.6. Sterically hindered amines, for example bis(2,2,6,6-tetramethyl-piperidyl)sebacate, bis(2,2,6,6-tetramethyl-piperidyl)succinate, bis(1,2,2,6,6-pentamethylpiperidyl)sebacate, bis(1,2,2,6,6-pentamethylpiperidyl) n-butyl-3,5-di-tert-butyl-4-hydroxybenzylmalonate, the condensate of 1-(2-hydroxyethyl)-2,2,6,6-tetramethyl-4-hydroxypiperidine and succinic acid, the condensate of N,N'-bis(2,2,6,6-tetramethyl-4-piperidyl)-hexamethylenediamine and 4-tert-octylamino-2,6-dichloro-1,3,5-triazine, tris(2,2,6,6-tetramethyl-4-piperidyl) nitrilotriacetate, tetrakis(2,2,6,6-tetramethyl-4- piperidyl)-1,2,3,4-butane-tetracarboxylate, 1,1'-(1,2-ethanediyl)bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl)malonate, 3-n-octyl-7,7,9,9-tetramethyl-1,3,8-triazasprio[4.5]decan-2,4-dion, bis(1-octyloxy-2,2,6,6-tetramethylpiperidyl)se bis(1-octyloxy-2,2,6,6-tetramethylpiperidyl)succinate, the condensate of N,N'-bis-(2,2,6,6-tetramethyl-4-piperidyl)hexamethylenediamine and 4-morpholino-2,6-dichloro-1,3,5-triazine, the condensate of 2-chloro-4,6-bis(4-n-butylamino-2,2,6,6-tetramethylpiperidyl )-1,3,5-triazine and 1,2-bis(3-aminopropylamino)ethane, the condensate of 2-chloro-4,6-di-(4-n-butylamino-1,2,2,6,6-pentamethylpiperidyl)-1,3,5-triazine and 1,2-bis-(3-aminopropylamino)ethane, 8-acetyl-3-dodecyl-7,7,9,9-tetramethyl- 1,3,8-triazaspiro[4.5]decane-2,4-dione, 3-dodecyl-1-(2,2,6,6-tetramethyl-4-piperidyl)pyrrolidin-2,5-dione, 3-dodecyl-1-(1,2,2,6,6-pentamethyl-4-piperidyl)pyrrolidine-2,5-dione.

2.7. Oxamides, for example 4,4'-dioctyloxyoxanilide, 2,2'-dioctyloxy-5,5'-di-tert-butoxanilide, 2,2'-didodecyloxy-5,5'-di-tert-butoxanilide, 2-ethoxy-2'-ethoxanilide, N,N'-bis(3-dimethylaminopropyl)oxamide, 2-ethoxy-5-tert-butyl-2'-ethoxanilide and its mixture with 2-ethoxy-2'-ethyl-5,4'-di-tert-butoxanilide and mixtures of ortho- and paramethoxy-disubstituted oxanilides and mixtures of o- and p-ethoxy-disubstituted oxanilides.

2.8. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-[2-hydroxy-4-(2hydroxy-3-butyloxy-propoxy)-phenyl]-4,6-bis(2,4-dimethyl)-1,3,5-triazine, 2-[2-hydroxy-4-(2-hydroxy-3-octyloxy-propyloxy)-phenyl]-4,6-bis(2,4-dimethyl)-1,3,5-triazine.

3. Metal deactivators, for example N,N'-diphenyloxamide, N-salicylal-N'-salicyloyl hydrazine, N,N'-bis(salicyloyl) hydrazine, N,N'-bis(3,5-di-tert-butyl-4-hydroxyphenylpropionyl) hydrazine, 3-salicyloylamino-1,2,4-triazole, bis(benzylidene)oxalyl dihydrazide, oxanilide, isophthaloyl dihydrazide, sebacoyl bisphenylhydrazide, N,N'-diacetyladipoyl dihydrazide, N,N'-bis(salicyloyl)oxalyl dihydrazide, N,N'-bis(salicyloyl)thiopropionyl dihydrazide.

4. Phosphites and phosphonites, for example triphenyl phosphite, diphenyl alkyl phosphites, phenyl dialkyl phosphites, tris(nonylphenyl) phosphite, trilauryl phosphite, trioctadecyl phosphite, distearyl pentaerythritol diphosphite, tris(2,4-di-tert-butylphenyl) phosphite, diisodecyl pentaerythritol diphosphite, bis(2,4-di-tert-butylphenyl) pentaerythritol diphosphite, bis(2,6-di-tert-butyl-4-methylphenyl)-pentaerythritol diphosphite, diisodecyloxypentaerythritol diphosphite, bis(2,4-di-tert-butyl-6-methylphenyl)pentaerythritol diphosphite, bis(2,4,6-tris(tert-butylphenyl)pentaerythritol diphsophite, tristearyl sorbitol triphosphite, tetrakis(2,4-di-tert-butylphenyl) 4,4'-biphenylene diphosphonite, 6-isooctyloxy-2,4,8,10-tetra-tert-butyl-12H-dibenz[d,g]-1,3,2-dioxaphosphocin, 6-fluoro-2,4,8,10-tetra-tert-butyl- 12-methyl-dibenz[d,g]-1,3,2-dioxaphosphocin, bis(2,4-di-tert-butyl-6-methylphenyl)methylphosphite, bis(2,4-di-tert-butyl-6-methylphenyl)ethylphosphite.

5. Peroxide scavengers, for example esters of β-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(β-dodecylmercapto)propionate.

6. Polyamide stabilisers, for example copper salts in combination with iodides and/or phosphorus compounds and salts of divalent manganese.

7. Basic co-stabilisers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example calcium stearate, zinc stearate, magnesium behenate, magnesium stearate, sodium ricinoleate and potassium palmitate, antimony pyrocatecholate or tin pyrocatecholate.

8. Nucleating agents, for example, 4-tert-butylbenzoic acid, adipic acid, diphenylacetic acid.

9. Fillers and reinforcing agents, for example, calcium carbonate, silicates, glass fibres, asbestos, talc, kaolin, mica, barium sulfate, metal oxides and hydroxydes, carbon black, graphite.

10. Other additives, for example, plasticisers, lubricants, emulsifiers, pigments, optical brighteners, flameproofing agents, antistatic agents and blowing agents.

The costabilisers are added, for example, in concentrations of 0.01 to 10%, relative to the total weight of the material to be stabilised.

Incorporation of the compounds of the formula (1) and, if desired, further additives into the polymeric, organic material is carried out by known methods, for example before or during moulding or else by applying the dissolved or dispersed compounds to the polymeric, organic material, if appropriate with subsequent slow evaporation of the solvent. The compounds of the formula (1) can also be added to the materials to be stabilised in the form of a masterbatch containing them, for example, in a concentration of 2.5 to 25% by weight.

The compounds of the formula (1) can also be added before or during polymerisation or before crosslinking.

The compounds of the formula (1) can be incorporated into the material to be stabilised in pure form or encapsulated in waxes, oils or polymers.

The compounds of the formula (1) can also be sprayed onto the polymer to be stabilised. They are capable of diluting other additives (for example the abovementioned customary additives) or melts thereof, as a result of which they can also be sprayed onto the polymer to be stabilised together with these additives. Addition by spraying during deactivation of the polymerisation catalysts, it being possible, for example, for the vapour used for deactivation to be used for spraying, is particularly advantageous.

In the case of bead-polymerised polyolefins, it may be advantageous, for example, to apply the compounds of the formula (1), if appropriate together with other additives, by spraying.

The materials thus stabilised can be used in various forms, for example as films, fibres, ribbons, moulded materials, profiles or as binders for paints, adhesives or cement.

In the preparation of polyurethanes, it is possible also to add water and/or highly volatile organic substances as blowing agents. Examples of suitable organic blowing agents are acetone, ethyl acetate, halogen-substituted alkanes, such as methylene chloride, chloroform, ethylidene chloride, vinylidene chloride, monofluorotrichlormethane, chlorodifluoromethane, dichlorodifluoromethane, furthermore butane, hexane, heptane or diethyl ether. A blowing effect can also be achieved by addition of compounds which decompose at temperatures above room temperature with the elimination of gases, for example of nitrogen, for example azo compounds such as azoisobutyronitrile.

The preparation of polyurethanes is advantageously carried out in the presence of suitable catalysts. The compounds used as such catalysts are catalysts known per se, for example tertiary amines, such as triethylamine, tributylamine, N-methylmorpholine, N-ethylmorpholine, N-cocomorpholine, N,N,N',N'-tetramethylethylenediamine, 1,4-diazabicyclo[2.2.2]octane, N-methyl-N'-dimethylaminoethylpiperazine, N,N-dimethylbenzylamine, bis(N,N-diethylaminoethyl) adipate, N,N-diethylbenzylamine, pentamethyldiethylenetriamine, N,N-dimethylcyclohexylamine, N,N,N',N'-tetramethyl-1,3-butanediamine, N,N-dimethyl-β-phenylethylamine, 1,2-dimethylimidazole and 2-methylimidazole, furthermore Mannich bases known per se and obtained from secondary amines, such as diethylamine, and aldehydes, preferably formaldehyde, or ketones, such as acetone, methyl ethyl ketone or cyclohexanone, and phenols, such as phenol, nonylphenol or bisphenol.

Examples of tertiary amines containing hydrogen atoms which are active towards isocyanate groups as catalysts are triethanolamine, triisopropanolamine, N-methyldiethanolamine, N-ethyldiethanolamine, N,N-dimethylethanolamine, and reaction products thereof with alkylene oxides, such as propylene oxide and/or ethylene oxide.

Further suitable catalysts are also silaamines containing carbon-silicone bonds, for example 2,2,4-trimethyl-2-silamorpholine and 1,3-diethylaminomethyltetramethyldisiloxane, furthermore nitrogen-containing bases, such as tetraalkylammonium hydroxides, furthermore alkali metal hydroxides, such as sodium hydroxide, alkali metal phenolates, such as sodium phenolate or alkali metal alcoholates, such as sodium methoxide, or hexahydrotriazines, furthermore organic metal compounds, in particular organic tin compounds, for example tin(II) salts of carboxylic acids, such as tin(II) acetate, tin(II) octoate, tin(II) ethylhexoate and tin(II) laurate, and tin(IV) compounds, for example dibutyltin oxide, dibutyltin dichloride, dibutyltin diacetate, dibutyltin dilaurate, dibutyltin maleate or dioctyltin diacetate. It is of course also possible to use all of the abovementioned catalysts as mixtures.

If desired, further additives known per se, for example surface-active additives, such as emulsifiers and foam stabilisers, may be present.

Examples of suitable emulsifiers are the sodium salts of castor oil sulfonates or salts of fatty acids with amines, such as diethylamine oleate or diethanolamine stearate. Alkali metal salts or ammonium salts of sulfonic acids, for example dodecylbenzenesulfonic acid or dinaphthylmethanedisulfonic acid, or of fatty acids, such as ricinolic acid, or of polymer fatty acids can also be used as surface-active additives.

Suitable foam stabilisers are in particular polyether siloxanes, specifically water-soluble representatives. In general, the structure of these compounds is such that an ethylene oxide/propylene oxide copolymer is linked to a polydimethylsiloxane radical.

Further additives which may be present in the compositions are reaction retarders, for example acidic substances, such as hydrochloric acid or organic acid halides, furthermore cell regulators of the type known per se, such as paraffins or fatty alcohols, or dimethylpolysiloxanes and pigments or dyes and flame retardants of the type known per se, for example tris(chloroethyl) phosphate, tricresyl phosphate or ammonium phosphate and ammonium polyphosphate, furthermore stabilisers against the effects of ageing and weather, plasticisers and substances acting as fungistats and bacteriostats and fillers, such as barium sulfate, kieselguhr, carbon black or precipitated chalk.

Further examples of surface-active additives and foam stabilisers and cell regulators, reaction retarders, stabilisers, flame retardants, plasticisers, dyes and fillers and substances acting as fungistats and bacteriostats which may be present and details on how these additives are used and on their mode of action are well known to one skilled in the art.

The polyurethane materials can be prepared in any desired form, for example in the form of fibres. However, it is preferred to prepare foams, a suitable selection of the components resulting either in elastic or rigid foam materials or in all products between these extremes.

Polyurethane foams are preferably prepared from liquid starting components, the starting materials to be reacted with one another being either mixed with one another in a one-step process or, alternatively, a preadduct containing NCO groups being first prepared from a polyol and an excess of polyisocyanate, which is then foamed, for example by reaction with water.

The reactants are made to react by the known one-step process, the prepolymer process or the semi prepolymer process, in which use is often made of mechanical equipment which is well known to the person skilled in the art.

In foam production, foaming is often carried out in moulds, the reaction mixture being introduced into a mould. Examples of suitable mould materials are metals, for example aluminium, or plastics, for example epoxy resin. In the mould, the foamable reaction mixture expands and forms the moulded article. Foam moulding can be carded out in such a manner that the moulded part exhibits cell structure at its surface, but it can also be carried out in such a manner that the moulded pan exhibits a compact skin and a cellular core. The procedure in this foam production can be such that the amount of foamable reaction mixture introduced into the mould is such that the resulting foam just about completely fills the mould. However, the procedure can also be such that more foamable reaction mixture is introduced into the mould than is necessary for completely filling the interior of the mould with foam. Accordingly, in the last-mentioned case, foam production takes place with "overcharging".

In foam moulding, the additional use of "external release agents" known per se, such as silicone oils, is very common. However, it is also possible to use so-called "internal release agents", if appropriate in the mixture with external release agents.

Cold-curing foams can also be produced. However, it is of course also possible to produce foams by block foaming or by the twin-belt method known per se.

It is also possible to produce flexible, semiflexible or rigid polyurethane foams. They are used as known per se for such products, for example as mattresses and upholstery in the furniture and automobile industries, furthermore for the production of dashboards such as are used in the automobile industry and finally as insulating materials and materials for heat insulation and low-temperature insulation, for example in the building sector or in the household refrigerator industry or in the textile industry, for example as shoulder pads.

The present invention also relates to a process for the stabilisation of an organic material against oxidative, thermal or light-induced degradation, which comprises incorporating therein or applying thereto at least one compound of the formula (1).

As already pointed out, the compounds according to the invention are also particularly advantageously used as stabilisers in polyolefins, in particular as thermal stabilisers. Excellent stabilisation is obtained, for example, by using them in combination with organic phosphites or phosphonites. In this combination, the advantage of the compounds according to the invention is that they are already active in extremely small amounts.

They are used, for example, in amounts of 0.0001 to 0.015, in particular 0.0001 to 0.008, % by weight, relative to the polyolefin. The organic phosphite or phosphonite is advantageously used in an amount of 0.01 to 2, in particular 0.01 to 1, % by weight, also relative to the polyolefin. The organic phosphites or phosphonites used are preferably those described in DE-A-4 202 276. See, in particular, the patent claims, the examples and pages 5, last paragraph, to page 11 of this publication. For particularly advantageous phosphites and phosphonites, see also item 4 of the above list of costabilisers.

The invention also relates to novel compounds of the formula (1)

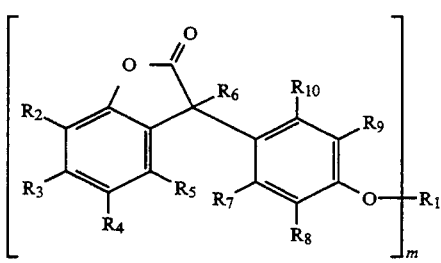

(1)

in which $R_2$, $R_3$, $R_4$ and $R_5$, independently of one another, are hydrogen, $C_1$-$C_{25}$alkyl, $C_7$-$C_9$phenylalkyl, unsubstituted or $C_1$-$C_4$alkyl-substituted phenyl, unsubstituted or $C_1$-$C_4$-alkyl-substituted $C_5$-$C_8$cycloalkyl; $C_1$-$C_{18}$alkoxy, hydroxyl, $C_1$-$C_{25}$alkanoyloxy, $C_3$-$C_{25}$-alkenoyloxy, $C_3$-$C_{25}$alkanoyloxy which is interrupted by oxygen, sulfur or >N—$R_{16}$; $C_6$-$C_9$-cycloalkylcarbonyloxy, benzoyloxy or $C_1$-$C_{12}$alkyl-substituted benzoyloxy, where $R_{16}$ is hydrogen or $C_1$-$C_8$alkyl, or, furthermore, the radicals $R_2$ and $R_3$ or the radicals $R_4$ and $R_5$ together with the carbon atoms to which they are bound form a phenyl ring, $R_4$ is additionally —(CH$_2$)$_n$—COR$_{11}$, in which n is 0, 1 or 2, $R_{11}$ is hydroxyl,

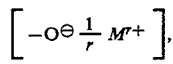

$C_1$-$C_{18}$alkoxy or

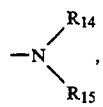

$R_{14}$ and $R_{15}$, independently of one another, are hydrogen or $C_1$-$C_{18}$alkyl, M is an r-valent metal cation and r is 1, 2 or 3, $R_7$, $R_8$, $R_9$ and $R_{10}$, independently of one another, are hydrogen, $C_1$-$C_4$alkyl or $C_1$-$C_4$alkoxy, with the proviso that at least one of the radicals $R_7$, $R_8$, $R_9$ and $R_{10}$ is hydrogen and, in the case where $R_3$, $R_5$, $R_6$, $R_7$ and $R_{10}$ are hydrogen, $R_4$ is additionally a radical of the formula (2)

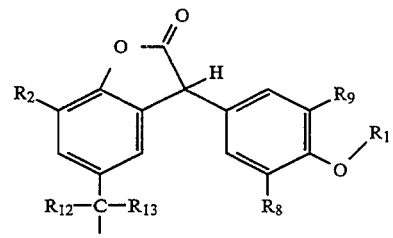

(2)

in which $R_2$, $R_8$ and $R_9$ are as defined above and $R_1$ is as defined below for m=1, and $R_{12}$ and $R_{13}$, independently of one another, are hydrogen, $C_1$-$C_{12}$alkyl or phenyl, m is 1 or 2, and, in the case where m is 1, $R_1$ is hydrogen, $C_1$-$C_{25}$alkanoyl, $C_3$-$C_{25}$alkenoyl, $C_3$-$C_{25}$alkanoyl which is interrupted by oxygen, sulfur or >N—$R_{16}$; $C_6$-$C_9$cycloalkylcarbonyl, benzoyl or $C_1$-$C_{12}$alkyl-substituted benzoyl, $R_{16}$ is as defined above and $R_6$ is hydrogen or a radical of the formula (3)

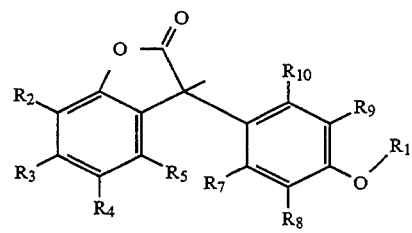

(3)

in which $R_1$, $R_2$, $R_3$, $R_4$, $R_5$, $R_7$, $R_8$, $R_9$ and $R_{10}$ are as defined above, and, in the case where m is 2, $R_1$ is

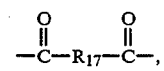

in which $R_{17}$ is a direct bond, $C_1$-$C_{18}$alkylene, $C_2$-$C_{18}$alkylene which is interrupted by oxygen, sulfur or >N—$R_{16}$; $C_2$-$C_{18}$alkenylene, $C_2$-$C_{20}$alkylidene, $C_7$-$C_{20}$phenylalkylidene, $C_5$-$C_8$cycloalkylene, $C_7$-$C_8$-bicycloalkylene or phenylene, $R_{16}$ is as defined above and $R_6$ is hydrogen, with the exclusion of the compounds of the formula (4) to (8)

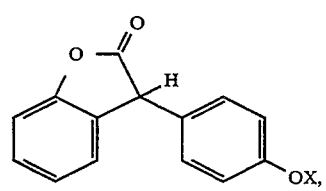

(4)

-continued

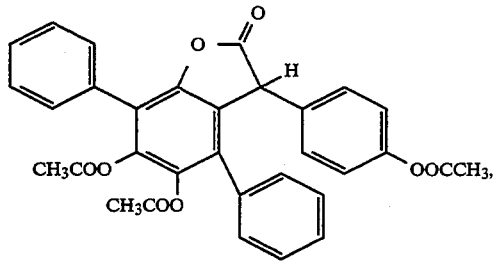 (5)

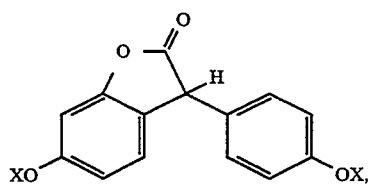 (6)

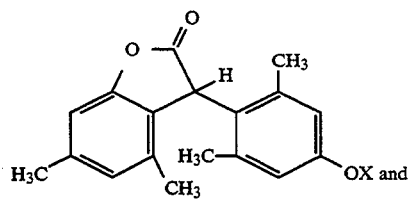 (7)

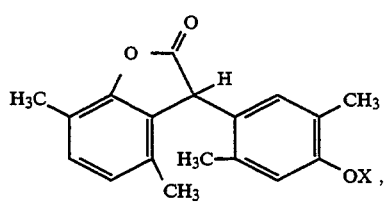 (8)

in which X is hydrogen or acetyl.

Preferred groups of novel compounds of the formula (1) conform to the preferences given above for the compositions according to the invention.

Preference is also given to compounds of the formula (1) in which $R_3$ and $R_5$ are hydrogen and at least one of the radicals $R_2$ and $R_4$ is not hydrogen.

Preference is also given to compounds of the formula (1) in which, in the case where m is 1, $R_1$ is $C_5$–$C_{25}$alkanoyl, $C_3$–$C_{25}$alkanoyl which is interrupted by oxygen, sulfur or >N—$R_{16}$; $C_5$–$C_8$cycloalkylcarbonyl, benzoyl or $C_1$–$C_{12}$alkyl-substituted benzoyl and $R_{16}$ is as defined above.

Particular preference is given to compounds of the formula (1) in which $R_2$ is hydrogen or $C_1$–$C_{14}$alkyl, $R_3$ and $R_5$ are hydrogen, $R_4$ is hydrogen, hydroxyl, $C_1$–$C_4$alkyl, $C_1$–$C_4$alkoxy or —$(CH_2)_n$—$COR_{11}$, in which n is 2 and $R_{11}$ is hydroxyl, $R_7$, $R_8$, $R_9$ and $R_{10}$, independently of one another, are hydrogen, $C_1$–$C_4$alkyl or $C_1$–$C_4$alkoxy, with the proviso that at least one of the radicals $R_7$, $R_8$, $R_9$ or $R_{10}$ is hydrogen, m is 1 and $R_1$ is hydrogen, $C_1$–$C_{18}$alkanoyl, $C_3$–$C_8$alkanoyl which is interrupted by oxygen; or is $C_3$–$C_4$alkenoyl and $R_6$ is hydrogen or a radical of the formula (3)

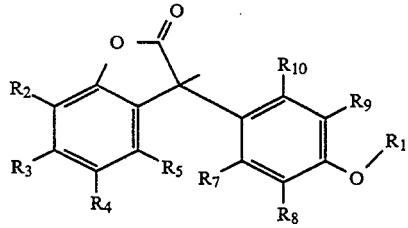 (3)

in which $R_1$, $R_2$, $R_3$, $R_4$, $R_5$, $R_7$, $R_8$, $R_9$ and $R_{10}$ are as defined above.

Very particular preference is given to compounds of the formula (1) in which $R_2$ is hydrogen or $C_1$–$C_{14}$alkyl, $R_3$, $R_5$, $R_6$, $R_7$ and $R_{10}$ are hydrogen, $R_4$ is hydrogen or $C_1$–$C_4$alkyl, $R_8$ and $R_9$, independently of one another, are hydrogen, $C_1$–$C_4$alkyl or $C_1$–$C_4$alkoxy, m is 1 and $R_1$ is $C_1$–$C_{10}$alkanoyl or $C_3$–$C_4$alkenoyl.

The compounds according to the invention of the formula (1) can be prepared in a manner known per se.

For example, this being the preferred procedure, a phenol of the formula (9)

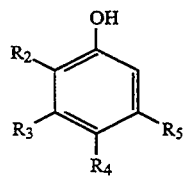 (9)

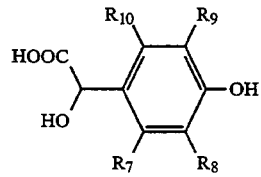 (10)

in which $R_2$, $R_3$, $R_4$ and $R_5$ are as defined above, is reacted with a 4-hydroxymandelic acid substituted on the phenyl ring and having the formula (10), in which $R_7$, $R_8$, $R_9$ and $R_{10}$ are as defined, at elevated temperature, in particular at temperatures of 130° to 200° C. in the melt or in a solvent, if appropriate under a slight vacuum. The reaction is preferably carried out in a solvent, for example acetic acid or formic acid, in a temperature range of from 50° to 130° C. The reaction can be catalysed by addition of an acid, such as hydrochloric acid, sulfuric acid or methanesulfonic acid. The reaction can be carried out, for example, in a manner such as described in the references given in the introduction of the description.

The 4-hydroxymandelic acids substituted on the phenyl ring are known in the literature or can be prepared analogously for example in accordance with W. Bradley et al., J. Chem. Soc. 1956, 1622; EP-A-146269 or DE 2 944 295.

The phenols of the formula (9) are also known or can be obtained by methods known per se.

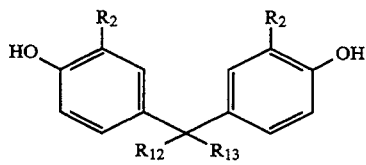

Bisphenol compounds of the formula (13) can be prepared in accordance with Houben-Weyl, Methoden der organischen Chemie (Methods of Organic Chemistry), volume 6/1c, 1030.

The phenols of the formula (1) obtained by this reaction, in which $R_1$ is hydrogen, can be esterified by generally known esterification methods, for example in accordance with Organikum 1986, page 402–408, for example by acylation with an acid chloride or acid anhydride of the formula $R_1{}^1Cl$ or $R_1{}^1$—O—$R_1{}^1$ in which $R_1{}^1$ is $R_1$ except hydrogen.

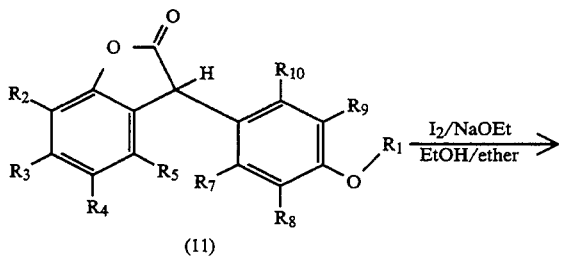

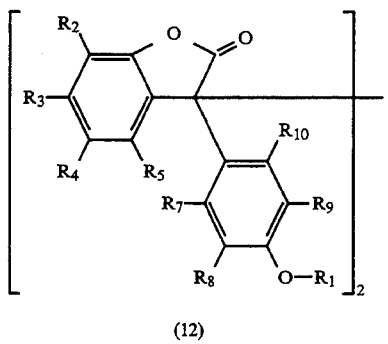

Dimerisation of the compounds of the formula (11) in order to prepare compounds of the formula (1) in which $R_6$ is a group of the formula (3) [compounds of the formula (12)] is carried out by oxidation with, for example, iodine under basic conditions in an organic solvent at room temperature. A suitable base in particular sodium ethoxide, and suitable solvents are ethanol and diethyl ether.

The examples which follow illustrate the invention in more detail. Parts or percentages given therein are by weight.

EXAMPLE 1

Preparation of 5,7-di-tert-butyl-3-(4-hydroxyphenyl)benzofuran-2-one (Compound (101), Table 1)

A mixture of 103.2 g (0.50 mol) of 2,4-di-tert-butylphenol and 102.4 g (0.55 mol) of 4-hydroxymandelic acid monohydrate in 100 ml of acetic acid is refluxed for 24 hours under a nitrogen atmosphere. The reaction mixture is then diluted with 140 ml of 50% aqueous acetic acid, cooled, and the precipitate formed is filtered off. The residue is washed with another 200 ml of 50% aqueous acetic acid and then dried, giving 95.9 g (57%) of 5,7-di-tert-butyl-3-(4-hydroxyphenyl)benzofuran-2-one, melting point 187°–190° C. (compound (101), Table 1).

EXAMPLE 2

Preparation of 3-(3,5-dimethyl-4-hydroxyphenyl)-5,7-di-tert-butylbenzofuran-2-one (Compound (107), Table 1)

1.5 ml (23 mmol) of methanesulfonic acid are added to a mixture of 154.8 g (0.75 mol) of 2,4-di-tert-butylphenol and 98.1 g (0.50 mol) of 3,5-dimethyl-4-hydroxymandelic acid in 500 ml of acetic acid which is stirred at 95° C. under nitrogen. After about 4 minutes, crystallisation of the product in the form of fine, white crystals begins. The reaction mixture is refluxed for another hour, then cooled to about 15° C., and the precipitated product is filtered off. The residue is washed with 250 ml of acetic acid and with 1500 ml of water. Drying gives 161.5 g (88%) of 3-(3,5-dimethyl-4-hydroxyphenyl)-5,7-di-tert-butylbenzofuran-2-one, melting point 225°–228° C. (compound (107), Table 1).

The compounds (102), (103), (104), (105), (106), (108), (116), (126), (128), (130), (131), (132) and (134) are prepared from the corresponding phenols and mandelic acids analogously to Example 2.

Procedure for the preparation of substituted 4-hydroxymandelic acids:

0.30 mol of starting phenol are dissolved in 150 ml of 2N sodium hydroxide solution under a nitrogen atmosphere. After cooling of the solution to +5° C., 4.8 g (0.12 mol) of sodium hydroxide and 13.3 ml (0.12 mol) of 50% aqueous glyoxylic acid are added, and the reaction mixture is stirred at room temperature for 4 hours. After 4 hours each, another 0.12 mol of sodium hydroxide and glyoxylic acid (a total of 0.36 mol) are added two more times. The reaction mixture is then additionally stirred for 12 hours, then neutralised with concentrated hydrochloric acid and washed twice with 75 ml of petroleum ether. The aqueous phase is then acidified with concentrated hydrochloric acid and extracted several times with ether. The organic phases are combined, dried over magnesium sulfate and concentrated on a vacuum rotary evaporator. In this manner, the following products are obtained: 3,5-dimethyl-4-hydroxymandelic acid, melting point 132°–135° C., yield 85%; 4-hydroxy-3-methylmandelic acid, melting point 115°–120° C., yield 55%; 4-hydroxy-3-tert-butylmandelic acid, melting point 156°–158° C., yield 26%; 3-isopropyl-4-hydroxy-2-methylmandelic acid, melting point 114°–119° C., yield 20%; 3,5-di-tert-butyl-4-hydroxymandelic acid, melting point 177°–180° C., yield 45%; and 3-methyl-5-tert-butyl-4-hydroxymandelic acid, melting point 138°–141° C., yield 50%.

EXAMPLE 3

Preparation of 3-(4-acetoxy-3,5-dimethylphenyl)-5,7-di-tert-butylbenzofuran-2-one (Compound (109), Table 1).

53.6 g (0.53 mol) of acetic anhydride are added dropwise over a period of about 10 minutes to a suspension of 183.3 g (0.50 mol) of 3-(3,5-dimethyl-4-hydroxyphenyl)-5,7-di-tert-butylbenzofuran-2-one (compound (107), Table 1, Example 2) in 250 ml of xylene and 0.5 ml (7.7 mmol) of methanesulfonic acid which is stirred at 105° C. under a nitrogen atmosphere. The clear, colourless reaction mixture is concentrated at about 170° C. under a slight vacuum. 500 ml of 1-butanol are carefully added to the residue and the mixture is cooled with ice/water. The precipitated product is filtered and washed with 100 ml of 1-butanol. Drying gives 197.6 g (97%) of 3-(4-acetoxy-3,5-dimethylphenyl)-5,7-di-tert-butylbenzofuran-2-one, melting point 165°–166° C. (compound (109), Table 1).

Compound (120) is prepared from compound (101) and compound (133) from compound (131) analogously to Example 3.

EXAMPLE 4

Preparation of 3-(3,5-dimethyl-4-pivaloyloxyphenyl)-5,7-di-tert-butyl-benzofuran-2-one (Compound (110), Table 1)

180.1 g (1.49 mol) of pivaloyl chloride are added dropwise over a period of 25 minutes to a suspension of 274.5 g (0.75 mol) of 3-(3,5-dimethyl-4-hydroxyphenyl)-5,7-di-tert-butylbenzofuran-2-one, (compound (107), Table 1, Example 2) in 600 ml of xylene and 7.5 ml (115.7 mmol) of methanesulfonic acid which is stirred at 95° C. under a nitrogen atmosphere. The clear, homogeneous reaction mixture is then refluxed for another 2.5 hours and then concentrated under a slight vacuum. 50 ml of 1-butanol and 600 ml of methanol are carefully poured into the liquid, hot residue at about 170° C. through the condenser and the mixture is cooled with ice/water. The precipitated product is filtered and washed with 350 ml of cold methanol. Drying gives 311.9 g (92%) of 3-(3,5-dimethyl-4-pivaloyloxyphenyl)-5,7-di-tert-butylbenzofuran-2-one, melting point 140°–142° C. (compound (110), Table 1).

The compounds (111), (112), (113), (114), (115), (117), (118), (119), (121), (122), (123), (124), (125) and (129) are prepared from the corresponding phenols and acid halides analogously to Example 4.

EXAMPLE 5

Preparation of 3,3'-bis[3-(3,5-dimethyl-4-pivaloyloxyphenyl)-5,7-di-tert-butylbenzofuran-2-one] (Compound (127), Table 1)

18.02 g (40 mmol) of 3-(3,5-dimethyl-4-pivaloyloxyphenyl)-5,7-di-tert-butylbenzofuran-2-one (compound (110), Example 4) are added under a nitrogen atmosphere to a sodium ethoxide solution prepared by addition of 0.92 g (40 mmol) of sodium to 80 ml of absolute ethanol. A solution of 5.08 g (20 mmol) of iodine in 50 ml of diethyl ether is then added dropwise at room temperature over a period of about 10 minutes. The reaction mixture is then additionally stirred for 5 minutes, 1.0 g (5.3 mmol) of sodium pyrosulfite is then added, and the mixture is diluted with 400 ml of water. The precipitate formed is extracted with methylene chloride. The organic phases are separated off, washed with water, combined, dried over sodium sulfate and concentrated on a vacuum rotary evaporator. Crystallisation of the residue from ethanol/methylene chloride gives 16.8 g (93%) of the 3,3'-bis[3(3,5-dimethyl-4-pivaloyloxyphenyl)-5,7-di-tert-butylbenzofuran-2-one], melting point 268°–270° C. (compound (127), Table 1).

TABLE 1

| No. | Compound | m.p. (°C.) | C (%), H (%) (calculated/found) | Yield (%) |
|---|---|---|---|---|
| 101 | [structure] | 187–190 | 78.07  7.74 / 78.04  7.84 | 57 |
| 102 | [structure] | 180–183 | 78.38  8.01 / 78.26  8.02 | 55 |
| 103 | [structure] | 191–201 (dcmp.) | Characterised by $^1$H-NMR in CDCl$_3$ δ(H*) = 4.77 ppm | 67 |

TABLE 1-continued

| No. | Compound | m.p. (°C.) | C (%), H (%) (calculated/found) | | Yield (%) |
|---|---|---|---|---|---|
| 104 | | 186–189 | 79.15  79.11 | 8.69  8.91 | 54 |
| 105 | | 186–189 | 77.39  77.36 | 7.14  7.18 | 54 |
| 106 | | 211–215 | 77.75  77.82 | 7.46  7.47 | 65 |
| 107 | | 225–228 | 78.65  78.68 | 8.25  8.38 | 88 |
| 108 | | oil | Characterised by $^1$H-NMR in CDCl$_3$ δ(H*) = 4.69 and 4.70 ppm (mixture of diastereomers) | | 46 |
| 109 | | 165–166 | 76.44  76.37 | 7.90  7.91 | 97 |

TABLE 1-continued

| No. | Compound | m.p. (°C.) | C (%), H (%) (calculated/found) | | Yield (%) |
|---|---|---|---|---|---|
| 110 | | 140–142 | 77.30<br>77.34 | 8.50<br>8.72 | 92 |
| 111 | | resin[a)] | 78.01<br>77.90 | 9.00<br>9.01 | 95 |
| 112 | | resin | 78.42<br>78.28 | 9.29<br>9.27 | 96 |
| 113 | | oil | Characterised by<br>$^1$H-NMR in CDCl$_3$<br>δ(H*) = 4.75 ppm | | 87 |
| 114 | | oil | Characterised by<br>$^1$H-NMR in CDCl$_3$<br>δ(H*) = 4.75 ppm | | 58 |
| 115 | | 142–145 | 73.95<br>73.92 | 7.81<br>8.01 | 45 |

TABLE 1-continued

| No. | Compound | m.p. (°C.) | C (%), H (%) (calculated/found) | | Yield (%) |
|---|---|---|---|---|---|
| 116 | | 175–189 | 72.23<br>72.56 | 6.85<br>7.13 | 30 |
| 117 | | 119–121 | 76.11<br>76.21 | 7.67<br>7.59 | 82 |
| 118 | | 143–145 | 76.44<br>76.65 | 7.90<br>7.85 | 79 |
| 119 | | oil | Characterised by $^1$H-NMR in CDCl$_3$ δ(H*) = 4.74 and 4.75 ppm (mixture of diastereomers) | | 70 |
| 120 | | 163–165 | 75.76<br>75.74 | 7.42<br>7.49 | 85 |
| 121 | | 136–142 | 76.74<br>76.77 | 8.11<br>8.31 | 73 |

TABLE 1-continued

| No. | Compound | m.p. (°C.) | C (%), H (%) (calculated/found) | | Yield (%) |
|---|---|---|---|---|---|
| 122 | | 147–149 | 77.21<br>77.60 | 9.07<br>8.97 | 65 |
| 123 | | 188–190 | Characterised by<br>$^1$H-NMR in CDCl$_3$<br>δ(H*) = 5.00 ppm | | 59 |
| 124 | | 130–135 | 77.39<br>77.20 | 7.89<br>8.07 | 33 |
| 125 | | 168–179 | Characterised by<br>$^1$H-NMR in CDCl$_3$<br>δ(H*) = 4.73 ppm | | 25 |
| 126 | | 158–164 | 71.82<br>71.38 | 5.67<br>5.74 | 16.5 |
| 127 | | 268–270 | 77.47<br>77.49 | 8.30<br>8.38 | 93 |

TABLE 1-continued

| No. | Compound | m.p. (°C.) | C (%), H (%) (calculated/found) | Yield (%) |
|---|---|---|---|---|
| 128 | | 221–226 | 71.10 5.22<br>70.90 5.33 | 15 |
| 129 | | 146–150 | 71.21 6.90<br>71.22 6.98 | 59 |
| 130 | | 157–160 | 74.97 7.66<br>74.92 7.72 | 50 |
| 131 | | 215–222 (dcmp.) | 79.37 8.88<br>79.16 8.97 | 88 |
| 132 | | 173–175 | 79.96 9.77<br>79.77 9.41 | 21 |
| 133 | | resin | 77.30 8.50<br>77.04 8.49 | 74 |

TABLE 1-continued

| No. | Compound | m.p. (°C.) | C (%), H (%) (calculated/found) | Yield (%) |
|---|---|---|---|---|
| 134 | [structure: benzofuranone with 3,5-dimethyl-4-hydroxyphenyl substituent] | 221–226 | 71.10  5.22<br>70.90  5.33 | 15 |

*a)* The octanoic acid used is a mixture of isomers

EXAMPLE 6

Stabilisation of Polypropylene in Multiple Extrusion 1.3 kg of polypropylene powder (Profax 6501) pre-stabilised with 0.025% of Irganox ® 1076 (n-octadecyl 3-[3,5-di-tert-butyl-4-hydroxyphenyl]propionate) (at a melt index of 3.2 measured at 230° C. and on 2.16 kg) are mixed with 0.05% of Irganox ® 1010 (pentaerythritol tetrakis[3-(3,5-di-tert-butyl-4-hydroxyphenyl)propionate], 0.05% of calcium stearate, 0.03% of dihydrotalcite (DHT 4A ®, Kyowa Chemical Industry Co., Ltd., [Mg$_{4.5}$Al$_2$(OH)$_{13}$CO$_3$.3.5H$_2$O]) and 0.015% of the compound from Table 1. This mixture is extruded in an extruder of cylinder diameter 20 mm and length 400 mm at 100 revolutions per minute, the 3 heating zones being set at the following temperatures: 260° C., 270° C. and 280° C. The extrudate is cooled by passing it through a waterbath and then granulated. These granules are repeatedly extruded. After 3 extrusions, the melt index is measured (at 230° C. on 2.16 kg). A large increase in the melt index indicates substantial chain degradation, i.e. poor stabilisation. The results are summarised in Table 2.

TABLE 2

| Compound from Table 1 | Melt index after 3 extrusions |
|---|---|
| — | 20.0 |
| 110 | 6.4 |
| 112 | 6.7 |
| 117 | 5.7 |
| 118 | 5.7 |
| 119 | 6.7 |
| 121 | 5.8 |
| 122 | 6.0 |

EXAMPLE 7

Stabilisation of Polyethylene During Processing 100 parts of polyethylene powder (Lupolen ® 5260 Z) are mixed with 0.05 part of pentaerythritol tetrakis[3-(3,5-di-tert-butyl-4-hydroxyphenyl)propionate], 0.05 part of tris(2,4-di-tert-butylphenyl) phosphite and 0.05 part of the compound from Table 1, and the mixture is kneaded at 220° C. and 50 revolutions per minute in a Brabender Plastograph. During this time, the resistance to kneading is continuously recorded as torque. During the kneading time, the polymer, after remaining constant for an extended period of time, begins to crosslink, which can be detected by a rapid increase in torque. In Table 3, the time until the substantial increase in torque is observed is given as a measure of stabiliser effect. The longer this time, the better the stabiliser effect.

TABLE 3

| Compound from Table 1 | Time until torque increases (min) |
|---|---|
| — | 9.0 |
| 110 | 18.0 |
| 112 | 16.5 |
| 117 | 21.0 |
| 118 | 18.5 |
| 119 | 19.0 |
| 121 | 23.0 |
| 122 | 19.0 |

EXAMPLE 8

Stabilisation of Thermoplastic Styrene-based Elastomers 70 g of styrene/butadiene/styrene (SBS, ®Finapren 416) are kneaded together with 0.25% of the stabiliser to be tested from Table 1 in a Brabender Plastograph at 200° C. and 60 revolutions per minute for 30 minutes. The induction time, i.e. the kneading time in minutes until torque increases by 1 Nm after the torque minimum, is determined from the shape of the torque curve. A large increase in induction time indicates good stabilisation. The results are summarised in Table 4.

TABLE 4

| Compound from Table 1 | Induction time in minutes |
|---|---|
| — | 5.0 |
| 109 | 12.1 |
| 110 | 12.0 |

EXAMPLE 9

Stabilisation of Polybutadiene Rubber 70 g of polymer (Buna CB 529 C) are kneaded together with 0.25% of the stabiliser to be tested from Table 1 in a Brabender Plastograph at 160° C. and 60 revolutions per minute for 30 minutes. The induction time, i.e. the kneading time in minutes until torque increases by 1 Nm after the torque minimum, is determined from the shape of the torque curve. A large increase in induction time indicates good stabilisation. The results are summarised in Table 5.

TABLE 5

| Compound from Table 1 | Induction time in minutes |
|---|---|
| — | 4.0 |
| 107 | 127.5 |

EXAMPLE 10

Stabilisation of a Polyether/polyurethane Flexible Foam 470 mg (0.3%, relative to the polyol) of a stabiliser mixture according to the invention (Table 6) are dissolved in 157 g of an antioxidant-free polyether polyol, ®Lupranol 2045, (trifunctional polyether polyol having primary hydroxyl groups; hydroxyl number 35 mg of KOH/g, water content below 0.1%, acid number below 0.1 mg of KOH/g). 10.24 g of a solution of 1.74 g of ®TECOSTAB [polysilicone from Goldschmidt, GER], 0.48 g of diazabicyclooctane [amine catalyst] and 0.8 g of water are added to the solution, and the mixture is vigorously stirred at 100 rpm for 60 seconds. 3.2 g of a solution of 0.32 g of tin octoate (catalyst) in 2.9 g of the above polyol are then added, and the mixture is again vigorously stirred at 100 rpm for 60 seconds. This is immediately followed by addition of 98 g of an isocyanate (®Lupranat T80 BASF; a mixture of 2,4- and 2,6-toluylene diisocyanate) with vigorous stirring, and, after 6 seconds, the mixture is poured into a lined mould. The exothermal temperature during foaming to give a foam block is measured. The foam blocks are cooled and stored at 5° C. in a conditioning cabinet for 24 hours. 2 cm thick discs are sawed off the centre of the blocks and from these round (cylindrical) test specimens are cut out by means of a drilling tool. The specimens are aged in a test tube with admission of air at 190° C. in a preheated aluminium block thermostat. Yellowing of these specimens is determined in accordance with ASTM D-1925 as Yellowness Index (YI). The later yellowing takes place and the smaller the Yellowness Index, the better the stabilisation. The results are summarised in Table 6.

TABLE 6

| Stabiliser mixture | Yellowness Index after oven ageing (0 to 160 min) | | | | | | | | | | |
|---|---|---|---|---|---|---|---|---|---|---|---|
| | 0 | 10 | 20 | 30 | 40 | 60 | 80 | 100 | 120 | 140 | 160 |
| — | −0.7 | 44 | 48 | 55 | 57 | 62 | | | | | |
| 0.24% of comp. 109 plus 0.06% of AO1 | −2 | 0 | 1.8 | 2.1 | 2.8 | 4.4 | 7.4 | 19 | 27 | 28 | 36 |
| 0.24% of comp. 109 plus 0.06% of AO2 | −2 | −0.3 | 0.2 | 0.5 | 1.3 | 2.9 | 4 | 15 | 28 | 30 | 38 |
| 0.24% of comp. 109 plus 0.06% of AO3 | −1.9 | −0.7 | −0.2 | 1.3 | 1.7 | 3.9 | 12 | 28 | 34 | 36 | 43 |

AO1 is a mixture of polyalkylated diphenylamines (® Irganox 5057)
AO2 is 4,4'-thiobis(6-tert-butyl-3-methylphenol)(® Santonox R)
AO3 is 2,2'-methylenebis(6-tert-butyl-4-methylphenol)

What is claimed is:
1. A composition comprising
   a) an organic material which is subject to oxidative, thermal or light-induced degradation and
   b) at least one compound of the formula(1)

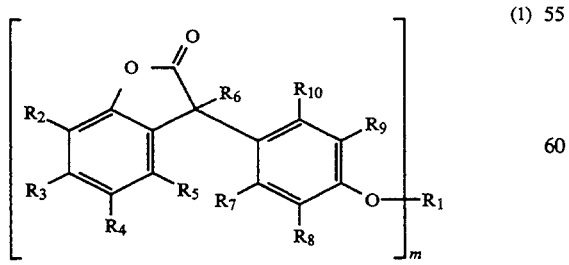

(1)

in which $R_2$, $R_3$, $R_4$ and $R_5$, independently of one another, are hydrogen, $C_1$-$C_{25}$alkyl, $C_7$-$C_9$phenylalkyl, unsubstituted or $C_1$-$C_4$alkyl-substituted phenyl, unsubstituted or $C_1$-$C_4$-alkyl-substituted $C_5$-$C_8$cycloalkyl; $C_1$-$C_{18}$alkoxy, hydroxyl, $C_1$-$C_{25}$alkanoyloxy, $C_3$-$C_{25}$alkenoyloxy, $C_3$-$C_{25}$alkanoyloxy which is interrupted by oxygen, sulfur or >N—$R_{16}$; $C_6$-$C_9$cycloalkylcarbonyloxy, benzoyloxy or $C_1$-$C_{12}$alkyl-substituted benzoyloxy, where $R_{16}$ is hydrogen or $C_1$-$C_8$alkyl, or, furthermore, the radicals $R_2$ and $R_3$ or the radicals $R_4$ and $R_5$ together with the carbon atoms to which they are bound form a phenyl ring, $R_4$ is additionally —$(CH_2)_n$—$COR_{11}$, in which n is 0, 1 or 2, $R_{11}$ is hydroxyl,

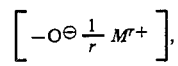

$C_1$-$C_{18}$alkoxy or

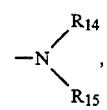

$R_{14}$ and $R_{15}$, independently of one another, are hydrogen or $C_1$-$C_{18}$alkyl, M is an r-valent metal cation and r is 1, 2 or 3, $R_7$, $R_8$, $R_9$ and $R_{10}$, independently of one another, are hydrogen, $C_1$-$C_4$alkyl or $C_1$-$C_4$alkoxy, with the proviso that at least one of the radicals $R_7$, $R_8$, $R_9$ and $R_{10}$ is hydrogen and, in the case where $R_3$, $R_5$, $R_6$, $R_7$ and $R_{10}$ are hydrogen, $R_4$ is additionally a radical of the formula (2)

(2)

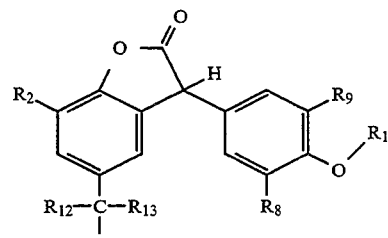

in which $R_2$, $R_8$ and $R_9$ are as defined above and $R_1$ is as defined below for m=1, and $R_{12}$ and $R_{13}$, independently of one another, are hydrogen, $C_1$-$C_{12}$alkyl or phenyl, m is 1 or 2, and,
in the case where m is 1,
$R_1$ is hydrogen, $C_1$-$C_{25}$alkanoyl, $C_3$-$C_{25}$alkenoyl, $C_3$-$C_{25}$alkanoyl which is interrupted by oxygen, sulfur or >N—$R_{16}$; $C_6$-$C_9$cycloalkylcarbonyl, benzoyl or $C_1$-$C_{12}$alkyl-substituted benzoyl, $R_{16}$ is as defined above and $R_6$ is hydrogen or a radical of the formula (3)

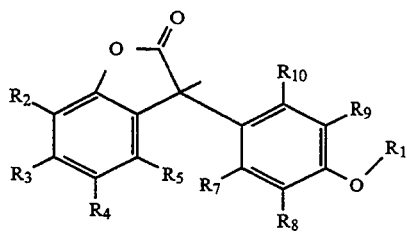

in which $R_1$, $R_2$, $R_3$, $R_4$, $R_5$, $R_7$, $R_8$, $R_9$ and $R_{10}$ are as defined above, and,
in the case where m is 2,
$R_1$ is

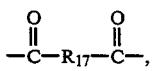

in which $R_{17}$ is a direct bond, $C_1$-$C_{18}$alkylene, $C_2$-$C_{18}$alkylene which is interrupted by oxygen, sulfur or >N—$R_{16}$; $C_2$-$C_{18}$alkenylene, $C_2$-$C_{20}$alkylidene, $C_7$-$C_{20}$phenylalkylidene, $C_5$-$C_8$cycloalkylene, $C_7$-$C_8$bicycloalkylene or phenylene, $R_{16}$ is as defined above and $R_6$ is hydrogen.

2. A composition according to claim 1, in which $R_2$, $R_3$, $R_4$ and $R_5$, independently of one another, are hydrogen $C_1$-$C_{18}$alkyl, benzyl, phenyl, $C_5$-$C_8$cycloalkyl, $C_1$-$C_8$alkoxy, hydroxyl, $C_1$-$C_{18}$alkanoyloxy, $C_3$-$C_{18}$alkenoyloxy or benzoyloxy, $R_4$ is additionally —(CH$_2$)$_n$—COR$_{11}$, and, in the case where m is 1, $R_1$ is hydrogen, $C_1$-$C_{18}$alkanoyl, $C_3$-$C_{18}$alkenoyl, $C_3$-$C_{18}$alkanoyl which is interrupted by oxygen, sulfur or >N—$R_{16}$; $C_6$-$C_9$cycloalkylcarbonyl, benzoyl or $C_1$-$C_8$alkyl-substituted benzoyl, $R_{16}$ is as defined above and, in the case where m is 2, $R_1$ is

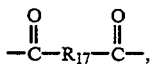

in which $R_{17}$ is a direct bond, $C_1$-$C_{12}$alkylene, $C_2$-$C_{12}$alkylene which is interrupted by oxygen, sulfur or >N—$R_{16}$; $C_2$-$C_{12}$alkenylene, $C_2$-$C_{12}$alkylidene, $C_7$-$C_{12}$phenylalkylidene, $C_5$-$C_8$cycloalkylene or phenylene and $R_{16}$ is as defined above.

3. A composition according to claim 1, in which at least two of the radicals $R_2$, $R_3$, $R_4$ and $R_5$ are hydrogen.

4. A composition according to claim 3, in which $R_3$ and $R_5$ are hydrogen.

5. A composition according to claim 1, in which $R_3$, $R_5$, $R_7$ and $R_{10}$, independently of one another, are hydrogen or $C_1$-$C_4$alkyl, $R_2$ is hydrogen or $C_1$-$C_{18}$alkyl, $R_4$ is hydrogen, $C_1$-$C_{12}$alkyl, $C_1$-$C_8$alkoxy, hydroxyl or —(CH$_2$)$_n$—COR$_{11}$, in which n is 0, 1 or 2, $R_{11}$ is hydroxyl or $C_1$-$C_{12}$alkoxy, and, in the case where m is 1, $R_1$ is hydrogen, $C_1$-$C_{18}$alkanoyl, $C_3$-$C_{18}$alkanoyl which is interrupted by oxygen; or $C_3$-$C_{18}$alkenoyl, and, in the case where m is 2, $R_1$ is

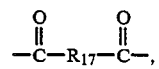

in which $R_{17}$ is $C_1$-$C_8$alkylene, $C_2$-$C_8$alkenylene, $C_2$-$C_8$alkylidene, $C_7$-$C_9$phenylalkylidene, cyclohexylene or phenylene.

6. A composition according to claim 1, in which $R_2$ is hydrogen or $C_1$-$C_{14}$alkyl, $R_3$ and $R_5$ are hydrogen, $R_4$ is hydrogen, hydroxyl, $C_1$-$C_4$alkyl, $C_1$-$C_4$alkoxy or —(CH$_2$)$_n$—COR$_{11}$, in which n is 2 and $R_{11}$ is hydroxyl, $R_7$, $R_8$, $R_9$ and $R_{10}$, independently of one another, are hydrogen, $C_1$-$C_4$alkyl or $C_1$-$C_4$alkoxy, with the proviso that at least one of the radicals $R_7$, $R_8$, $R_9$ or $R_{10}$ is hydrogen, m is 1 and $R_1$ is hydrogen, $C_1$-$C_{18}$alkanoyl, $C_3$-$C_8$alkanoyl which is interrupted by oxygen; or is $C_3$-$C_4$alkenoyl and $R_6$ is hydrogen or a radical of the formula (3)

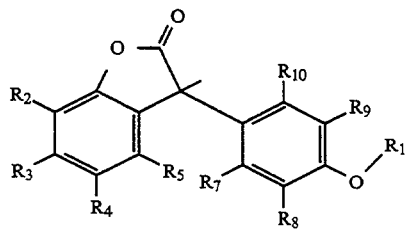

in which $R_1$, $R_2$, $R_3$, $R_4$, $R_5$, $R_7$, $R_8$, $R_9$ and $R_{10}$ are as defined above.

7. A composition according to claim 1, in which $R_2$ is hydrogen or $C_1$-$C_{14}$alkyl, $R_3$, $R_5$, $R_6$, $R_7$ and $R_{10}$ are hydrogen, $R_4$ is hydrogen or $C_1$-$C_4$alkyl, $R_8$ and $R_9$, independently of one another, are hydrogen, $C_1$-$C_4$alkyl or $C_1$-$C_4$alkoxy, m is 1 and $R_1$ is $C_1$-$C_{10}$alkanoyl or $C_3$-$C_4$alkenoyl.

8. A composition according to claim 1, in which component a) is a synthetic polymer.

9. A composition according to claim 1, in which component b) is present in an amount of 0.0005 to 5%, relative to the weight of component a).

10. A composition according to claim 1, additionally containing an organic phosphite or phosphonite.

11. A process for the stabilisation of an organic material against oxidative, thermal or light-induced degradation, which comprises incorporating therein or applying thereto at least one compound of the formula (1) defined in claim 1.

* * * * *